US008594836B2

(12) United States Patent  (10) Patent No.: US 8,594,836 B2
Hamada et al.  (45) Date of Patent: Nov. 26, 2013

(54) SAMPLE PROCESSING SYSTEM, SAMPLE PROCESSING METHOD, AND COMPUTER PROGRAM PRODUCT

(75) Inventors: Yuichi Hamada, Kobe (JP); Keisuke Kuwano, Kobe (JP)

(73) Assignee: Sysmex Corporation, Hyogo (JP)

( * ) Notice: Subject to any disclaimer, the term of this patent is extended or adjusted under 35 U.S.C. 154(b) by 887 days.

(21) Appl. No.: 12/639,413

(22) Filed: Dec. 16, 2009

(65) Prior Publication Data

US 2010/0152890 A1  Jun. 17, 2010

(30) Foreign Application Priority Data

Dec. 17, 2008  (JP) ................................. 2008-320584

(51) Int. Cl.
*G06F 7/00*  (2006.01)
(52) U.S. Cl.
USPC ......................................................... 700/228
(58) Field of Classification Search
USPC .................................................. 700/228, 213
See application file for complete search history.

(56) References Cited

U.S. PATENT DOCUMENTS

| 6,019,945 A | 2/2000 | Ohishi et al. | |
|---|---|---|---|
| 2001/0025207 A1* | 9/2001 | Soraoka et al. | 700/228 |
| 2005/0036913 A1 | 2/2005 | Yamakawa et al. | |
| 2010/0129789 A1* | 5/2010 | Self et al. | 435/5 |

FOREIGN PATENT DOCUMENTS

| JP | 10-325839 A | 12/1998 |
|---|---|---|
| JP | 2001-349897 A | 12/2001 |

* cited by examiner

*Primary Examiner* — Ramya Burgess
(74) *Attorney, Agent, or Firm* — Brinks Gilson & Lione

(57) ABSTRACT

A sample processing system comprising: a transporting apparatus for transporting samples to a first loading position, a second loading position, and a third loading position; a first sample processing apparatus capable of being set in a first setting position and a third setting position; a second sample processing apparatus capable of being set in a second setting position; and a controller including a memory under control of a processor, the memory storing instructions enabling the processor to carry out operations comprising: controlling the transporting apparatus so as to transport a sample to the first loading position when the first sample processing apparatus is set in the first setting position; and controlling the transporting apparatus so as to transport a sample to the third loading position when the first sample processing apparatus is set in the third setting position, is disclosed. A sample processing method and a computer program product are also disclosed.

17 Claims, 25 Drawing Sheets

SAMPLE PROCESSING SYSTEM, SAMPLE PROCESSING METHOD, AND COMPUTER PROGRAM PRODUCT

RELATED APPLICATIONS

This application claims priority under 35 U.S.C. §119 to Japanese Patent Application No. JP2008-320584 filed on Dec. 17, 2008, the entire content of which is hereby incorporated by reference.

FIELD OF THE INVENTION

The present invention relates to a sample processing system, a sample processing method, and a computer program product. The present invention particularly relates to: a sample processing system including a plurality of sample processing apparatuses; a sample processing method using the plurality of sample processing apparatuses; and a computer program product for controlling the plurality of sample processing apparatuses.

BACKGROUND OF THE INVENTION

Conventionally, there is a known sample processing system including a plurality of sample processing apparatuses.

JP laid-open patent 2000-028620 and JP laid-open patent 2001-349897 each disclose a multiple-sample analysis system (a sample processing system) that includes: a plurality of analyzers (sample processing apparatuses) that are arranged so as to be adjacent to each other; and rack transporting means (a transporting apparatus) for transporting samples to the plurality of analyzers.

In such a sample processing system that includes a plurality of analyzers, there is a case where maintenance work is performed on side faces, of adjoining analyzers, which are opposed to each other. In such a case, it is necessary to widen a space between the adjoining analyzers in order to obtain sufficient space for the maintenance work. However, the overall size of such a sample processing system is required to be reduced. Accordingly, in some cases, in order to perform maintenance work on one of the side faces, of the adjoining analyzers, which are opposed to each other, moving only an analyzer that is subjected to the maintenance work is not enough to obtain sufficient space for the maintenance work, and the other analyzer which is operating normally and which does not need maintenance at the time also needs to be moved.

However, when it is necessary in the sample processing systems of JP laid-open patent 2000-028620 and JP laid-open patent 2001-349897 to move the normally operating analyzer as described above, there is a necessity to stop the sample processing that is being performed by the normally operating analyzer and then move the analyzer. Thus, it is impossible to continue the sample processing while obtaining sufficient space for the maintenance work.

SUMMARY OF THE INVENTION

The scope of the invention is defined solely by the appended claims, and is not affected to any degree by the statements within this summary.

A first aspect of the present invention is a sample processing system comprising: a transporting apparatus for transporting samples to a first loading position, a second loading position, and a third loading position; a first sample processing apparatus capable of being set in a first setting position and a third setting position, wherein when the first sample processing apparatus is set in the first setting position, the first sample processing apparatus is capable of being loaded with the sample having been transported to the first loading position and processing the loaded sample, and when the first sample processing apparatus is set in the third setting position, the first sample processing apparatus is capable of being loaded with the sample having been transported to the third loading position and processing the loaded sample; a second sample processing apparatus capable of being set in a second setting position, wherein when the second sample processing apparatus is set in the second setting position, the second sample processing apparatus is capable of being loaded with the sample having been transported to the second loading position and processing the loaded sample; and a controller including a memory under control of a processor, the memory storing instructions enabling the processor to carry out operations comprising: controlling the transporting apparatus so as to transport a sample to the first loading position when the first sample processing apparatus is set in the first setting position; and controlling the transporting apparatus so as to transport a sample to the third loading position when the first sample processing apparatus is set in the third setting position.

A second aspect of the present invention is a sample processing method comprising: transporting a sample to a first loading position; performing loading and processing, of the sample having been transported to the first loading position, by a first sample processing apparatus that is set in a first setting position; transporting a sample to a second loading position; performing loading and processing, of the sample having been transported to the second loading position, by a second sample processing apparatus that is set in a second setting position; transporting a sample to a third loading position when the first sample processing apparatus is set in a third setting position; and performing loading and processing, of the sample having been transported to the third loading position, by the first sample processing apparatus set in the third setting position.

A third aspect of the present invention is a computer program product for a sample processing system comprising: a transporting apparatus for transporting samples; a first sample processing apparatus for being loaded with and processing a sample; a second sample processing apparatus for being loaded with and processing a sample; and a computer, the computer program product comprising a computer readable medium for storing instructions enabling the computer to carry out operations comprising: controlling the transporting apparatus so as to transport a sample to a first loading position; controlling the first sample processing apparatus set in a first setting position such that the first sample processing apparatus is loaded with the sample having been transported to the first loading position and processes the loaded sample; controlling the transporting apparatus so as to transport a sample to a second loading position; controlling the second sample processing apparatus set in a second setting position such that the second sample processing apparatus is loaded with the sample having been transported to the second loading position and processes the loaded sample; controlling the transporting apparatus so as to transport a sample to a third loading position when the first sample processing apparatus is set in a third setting position; and controlling the first sample processing apparatus set in the third setting position, such that the first sample processing apparatus is loaded with the sample having been transported to the third loading position and processes the loaded sample.

DETAILED DESCRIPTION OF THE PREFERRED EMBODIMENTS

Hereinafter, an embodiment of a sample processing system of the present invention will be described in detail with reference to the accompanying drawings.

Figure 1:
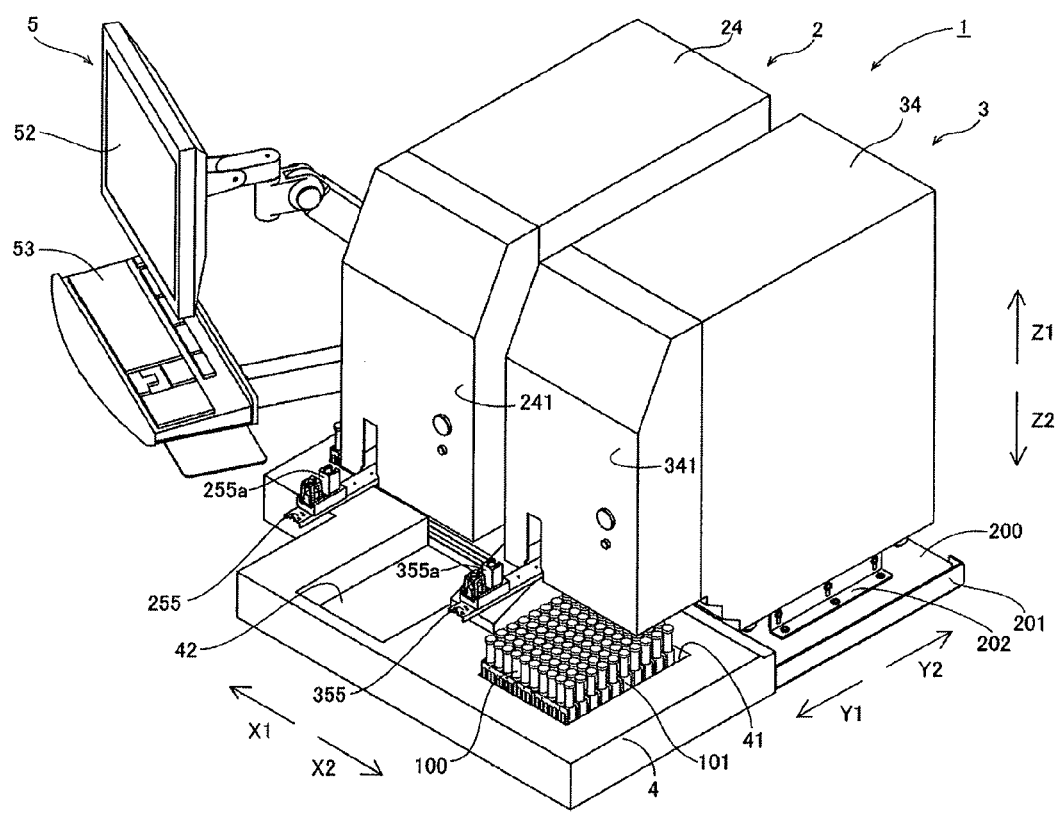
FIG. 1 is a perspective view showing an overall configuration of a blood analyzer according to an embodiment of the present invention.

FIG. 1 is a perspective view showing an overall structure of a blood analyzer according to the embodiment of the present invention. FIGS. 2 to 12 each illustrate, in detail, components of the blood analyzer according to the embodiment shown in FIG. 1. First, an overall structure of a blood analyzer 1 according to the embodiment of the present invention will be described with reference to FIGS. 1 to 12. Note that the present embodiment describes a case where the present invention is applied in the blood analyzer that is an example of the sample processing system.

As shown in FIG. 1, the blood analyzer 1 according to the present embodiment includes: two measurement units that are a first measurement unit 3 disposed on an upstream side of a transporting direction in which a sample is transported toward a below-described analyzed rack holder 42 (i.e., disposed on an arrow X2 direction side) and a second measurement unit 2 disposed on a downstream side of the transporting direction in which the sample is transported toward the analyzed rack holder 42 (i.e., disposed on an arrow X1 direction side); a sample transporting apparatus (sampler) 4 disposed in front of the first measurement unit 3 and the second measurement unit 2 (i.e., disposed on an arrow Y1 direction side); and a control apparatus 5 structured as a PC (Personal Computer) that is electrically connected to the first measurement unit 3, the second measurement unit 2, and the sample transporting apparatus 4. Further, the blood analyzer 1 is connected to a host computer 6 (see FIG. 2) via the control apparatus 5.

Figure 2:
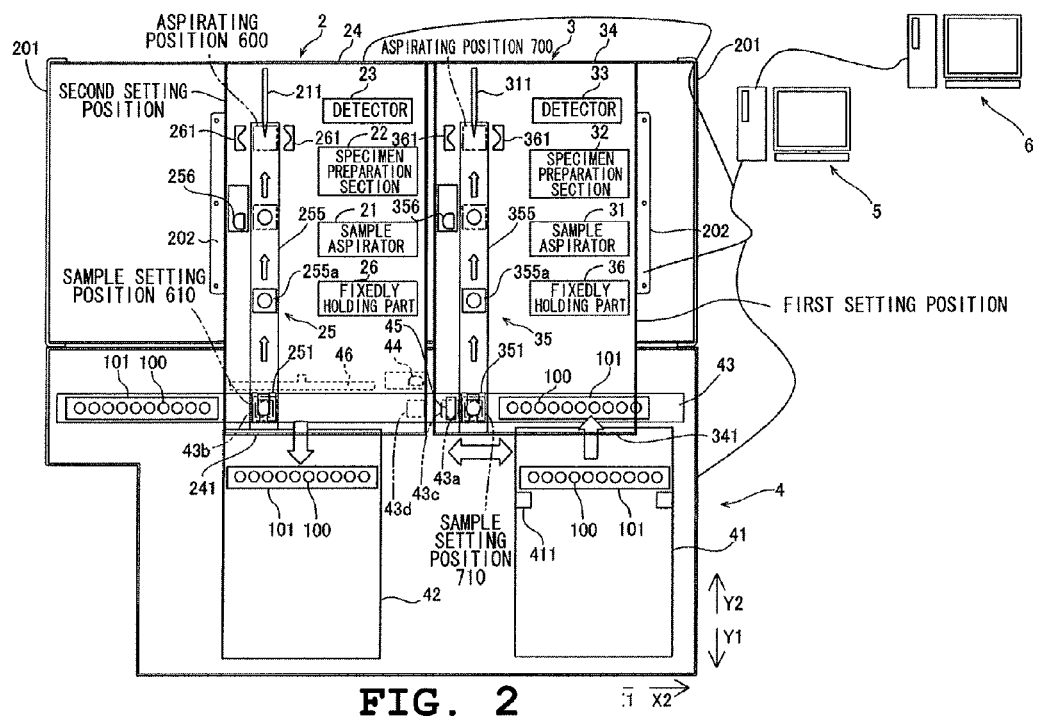
FIG. 2 is a schematic diagram showing measurement units and a sample transporting apparatus of the blood analyzer according to the embodiment shown in FIG. 1.
Figure 3:
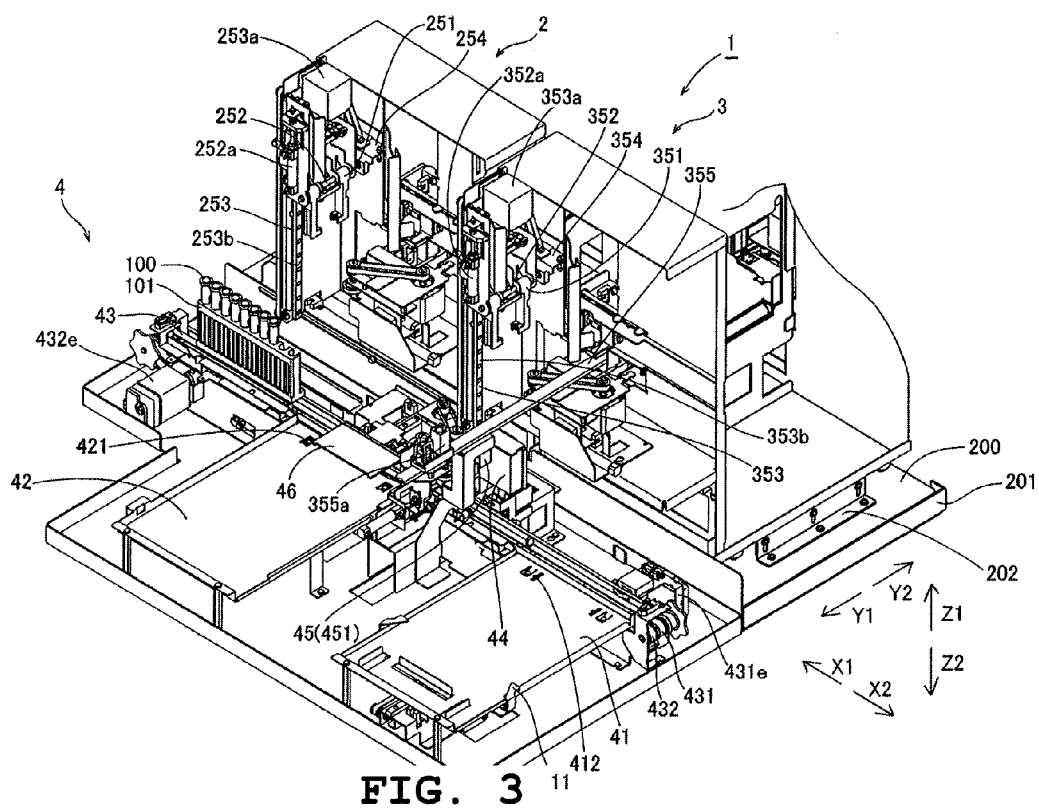
FIG. 3 is a perspective view showing the measurement units and the sample transporting apparatus of the blood analyzer according to the embodiment shown in FIG. 1.

Further, as shown in FIGS. 1 to 3, the first measurement unit 3 and the second measurement unit 2 are measurement units of practically the same type, which are arranged so as to be adjacent to each other. To be specific, in the present embodiment, the second measurement unit 2 uses the same measurement principle as that of the first measurement unit 3 to measure a sample for the same measurement item as that of the first measurement unit 3. The second measurement unit 2 further performs measurement for measurement items for which the first measurement unit 3 does not perform measurement. As shown in FIG. 2, the second measurement unit 2 includes: a sample aspirator 21 for aspirating a blood sample from a sample container (test tube) 100; a specimen preparation section 22 for preparing a detection specimen from the blood aspirated by the sample aspirator 21; and a detector 23 for detecting blood cells from the detection specimen prepared by the specimen preparation section 22. Also, the first measurement unit 3 includes: a sample aspirator 31 for aspirating a blood sample from a sample container (test tube) 100; a specimen preparation section 32 for preparing a detection specimen from the blood aspirated by the sample aspirator 31; and a detector 33 for detecting blood cells from the detection specimen prepared by the specimen preparation section 32.

As shown in FIG. 2, the second measurement unit 2 further includes: a unit cover 24 for accommodating therein the sample aspirator 21, the specimen preparation section 22, and the like; a sample container transporter 25 for loading a sample container 100 into the inside of the unit cover 24 and for transporting the sample container 100 to an aspirating position 600 of the sample aspirator 21; and a fixedly holding part 26 for fixedly holding the sample container 100 in the aspirating position 600. Also, the first measurement unit 3 further includes: a unit cover 34 for accommodating therein the sample aspirator 31, the specimen preparation section 32, and the like; a sample container transporter 35 for loading a sample container 100 into the inside of the unit cover 34 and for transporting the sample container 100 to an aspirating position 700 of the sample aspirator 31; and a fixedly holding part 36 for fixedly holding the sample container 100 in the aspirating position 700.

As shown in FIG. 2, the sample aspirator 21 (31) includes a piercer 211 (311). The tip of the piercer 211 (311) is formed so as to be able to penetrate (pierce) through a below-described sealing cap 100a (see FIG. 4) of the sample container 100. Further, the piercer 211 (311) is configured to move in vertical directions (arrow Z1 and Z2 directions) through an operation of a piercer drive section that is not shown.

The detector 23 (33) is configured to perform RBC detection (detection of red blood cells) and PLT detection (detection of platelets) by the sheath flow DC detection method, and to perform HGB detection (detection of hemoglobin in blood) by the SLS-hemoglobin method. The detector 23 (33) is also configured to perform WBC detection (detection of while blood cells) by flow cytometry using semiconductor laser. Detection results obtained by the detector 23 (33) are transmitted to the control apparatus 5 as measurement data (measurement results) of the sample. Note that the measurement data is used as a basis for final analysis results provided to a user (such as a red blood count, platelet count, amount of hemoglobin, white blood count, and the like).

As shown in FIG. 3, the sample container transporter 25 (35) has: a hand part 251 (351) capable of holding a sample container 100; an opening/closing part 252 (352) capable of opening/closing the hand part 251 (351); a vertically moving part 253 (353) for rectilinearly moving the hand part 251 (351) in vertical directions (the arrow Z1 and Z2 directions); and an agitator 254 (354) for moving the hand part 251 (351) in the vertical directions (the arrow Z1 and Z2 directions) in a swinging manner. Further, as shown in FIG. 2, the sample container transporter 25 (35) has: a sample container moving part 255 (355) for horizontally moving the sample container 100 in the arrow Y1 and Y2 directions; and a bar code reader 256 (356).

The hand part 251 (351) is disposed above a transporting path on which a rack 101 is transported by the sample transporting apparatus 4. The hand part 251 (351) is configured to, when a sample container 100 has been transported by the sample transporting apparatus 4 to a below-described second loading position 43b (first loading position 43a) (see FIG. 2), move downward (in the arrow Z2 direction) and then be caused by the opening/closing part 252 (352) to open and close to hold the sample container 100 accommodated in the rack 101.

Further, the hand part 251 (351) is configured to move the held sample container 100 upward (in the arrow Z1 direction) to remove the sample container 100 from the rack 101, and then be moved in a swinging manner by the agitator 254 (354) (e.g., 10 reciprocatory swinging movements). In this manner, the hand part 251 (351) is capable of agitating the blood contained in the held sample container 100. The hand part 251 (351) is configured to move, after the agitation has ended, downward (in the arrow Z2 direction) and then be caused by the opening/closing part 252 (352) to release the holding of the sample container 100. To be specific, the hand part 251 (351) is configured to set the sample container 100 into a sample setting part 255a (355a) that has been moved by the sample container moving part 255 (355) so as to be disposed in a sample setting position 610 (710) (see FIG. 2). Note that as shown in FIG. 2, the second loading position 43b and the sample setting position 610 coincide with each other when viewed in a plan view. Also, the first loading position 43a and the sample setting position 710 coincide with each other when viewed in a plan view.

The opening/closing part 252 (352) is configured to cause, based on the dynamics of an air cylinder 252a (352a), the hand part 251 (351) to open and close so as to hold the sample container 100.

The vertically moving part 253 (353) is configured to move, based on the dynamics of a stepping motor 253a (353a), the hand part 251 (351) along a rail 253b (353b) in the vertical directions (the arrow Z1 and Z2 directions).

The agitator 254 (354) is configured to move the hand part 251 (351) in the vertical directions (the arrow Z1 and Z2 directions) in a swinging manner based on the dynamics of a stepping motor that is not shown.

As shown in FIGS. 1 and 3, the sample container moving part 255 (355) has the sample setting part 255a (355a), and is capable of moving the sample setting part 255a (355a) to predetermined positions in accordance with operations performed during a measurement process. To be specific, the sample container moving part 255 (355) is capable of disposing the corresponding sample setting part in the aspirating position 600 (700) shown in FIG. 2, and disposing the corresponding sample setting part in the sample setting position 610 (710) shown in FIG. 2.

The bar code reader 256 (356) is configured to read a bar code 100b (shown in FIG. 4) affixed to each sample container 100. The bar code 100b of each sample container 100 is uniquely assigned to the sample therein, and used to manage analysis results of each sample.

The fixedly holding part 26 (36) is configured to fixedly hold a sample container 100 having been moved to the aspirating position 600 (700). To be specific, as shown in FIG. 2, the fixedly holding part 26 (36) has a pair of chuck parts 261 (361). The pair of chuck parts 261 (361) are configured to move closer toward each other so as to hold the sample container 100 therebetween.

Figure 5:
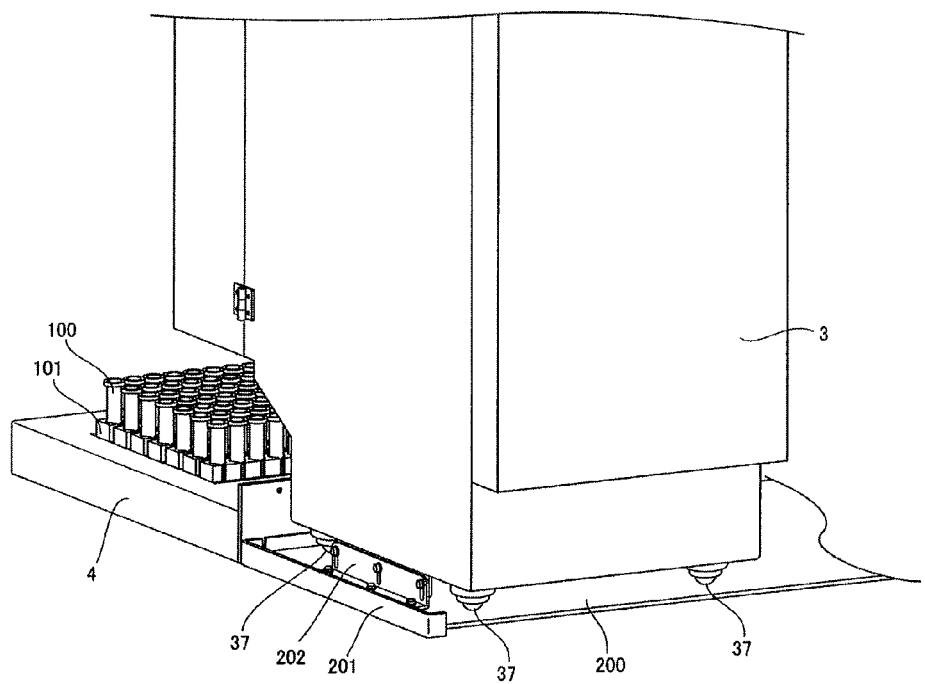
FIG. 5 is a perspective view illustrating a base of the blood analyzer according to the embodiment shown in FIG. 1.
Figure 6:
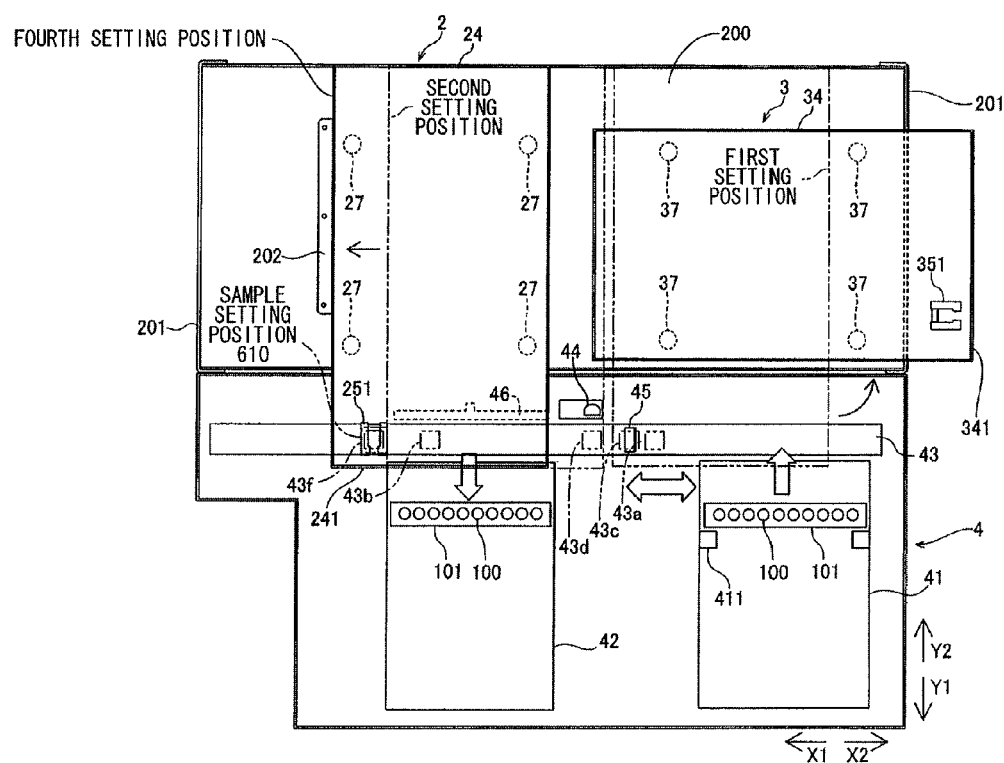
FIG. 6 is a schematic diagram illustrating configurations of the measurement units of the blood analyzer according to the embodiment shown in FIG. 1.
Figure 7:
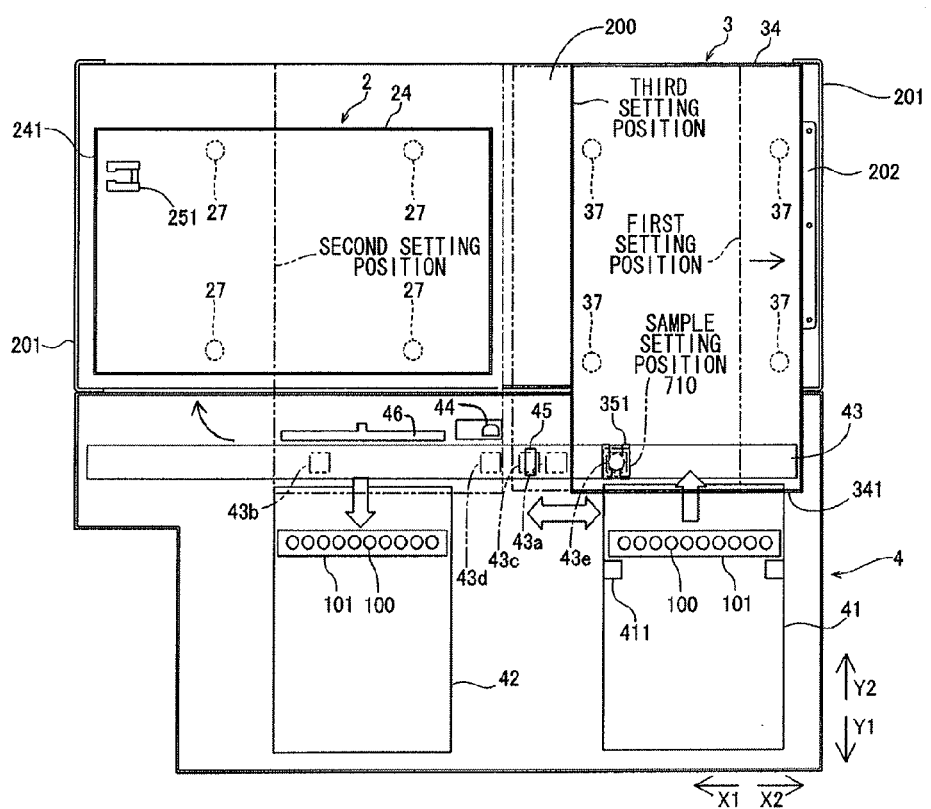
FIG. 7 is a schematic diagram illustrating configurations of the measurement units of the blood analyzer according to the embodiment shown in FIG. 1.

As shown in FIGS. 5 to 7, the second measurement unit 2 and the first measurement unit 3 have four casters 27 and four casters 37, respectively, on the bottom faces thereof, and are thereby configured to be able to move on a base 200. Accordingly, it is possible to obtain work space between the first measurement unit 3 and the second measurement unit 2 by widening a distance therebetween. Further, the base 200 has side face guides 201 at both side faces thereof (a side face on the arrow X1 direction side and a side face on the arrow X2 direction side), respectively, and has a top face guide (not shown) on the top face thereof. Accordingly, as shown in FIG. 6, the first measurement unit 3 can be rotated, while being prevented from falling off the base 200, such that a front face 341 thereof faces in the arrow X2 direction. Further, as shown in FIG. 7, the second measurement unit 2 can be rotated, while being prevented from falling off the base 200, such that a front face 241 thereof faces in the arrow X1 direction. Owing to the above configuration, maintenance work can be readily performed on side faces, of the first measurement unit 3 and the second measurement unit 2, which are opposed to each other.

As shown in FIG. 2 and FIG. 5, the first measurement unit 3 and the second measurement unit 2 are each configured to be fixed to the base 200 by a side face fixing member 202. The side face fixing members 202 are configured to fix the first measurement unit 3 and the second measurement unit 2 to the base 200 in their normal mode setting positions shown in FIG. 2 (a first setting position and a second setting position), respectively, in which the first measurement unit 3 and the second measurement unit 2 both operate normally. As shown in FIG. 7, the side face fixing member 202 is configured to be able to fix the first measurement unit 3 to the base 200 in a third setting position that is shifted, by a distance equivalent to four sample containers 100 held in the rack 101, from the first setting position of the normal mode in the arrow X2 direction (a direction away from the second setting position). Further, as shown in FIG. 6, the side face fixing member 202 is configured to be able to fix the second measurement unit 2 to the base 200 in a fourth setting position that is shifted, by a distance equivalent to four sample containers 100 held in the rack 101, from the second setting position of the normal mode in the arrow X1 direction (a direction away from the first setting position). Note that the first measurement unit 3 and the second measurement unit 2 are capable of performing sample processing in the third setting position and in the fourth setting position, respectively, during a maintenance measurement mode that is described later.

As described below, the third setting position is set as a position in which all the sample containers 100 in the rack 101 transported by the rack transporter 43 can be loaded into the first measurement unit 3. The same is true for the fourth setting position and the second measurement unit 2. To be specific, when the rack 101 is disposed, on the rack transporter 43, at the end of the upstream side of the transporting direction (i.e., at the end of the arrow X2 direction side), the first measurement unit 3 in the third setting position can be loaded with a sample container 100 that is held, in the rack 101, at the end of the downstream side of the transporting direction (at the end of the arrow X1 direction side of the rack 101). Similarly, when the rack 101 is disposed, on the rack transporter 43, at the end of the downstream side of the transporting direction (i.e., at the end of the arrow X1 direction side), the second measurement unit 2 in the fourth setting position can be loaded with a sample container 100 that is held, in the rack 101, at the end of the upstream side of the transporting direction (at the end of the arrow X2 direction side of the rack 101). A moving distance from the first setting position to the third setting position, and a moving distance from the second setting position to the fourth setting position, are each equivalent to a distance of maximum movement, of one measurement unit (measurement unit that is to continue the measurement), in a direction away from the other measurement unit (measurement unit that is a subject of maintenance work), the movement being in such a range as to allow all the sample containers 100 held in the rack 101 to be loaded into the one measurement unit. In the present embodiment, this distance is equivalent to four sample containers held in the rack 101. In this manner, the one measurement unit having been moved (the measurement unit that is to continue the measurement) can perform sample processing with the same sample processing capability as in a proper position (the first setting position or the second setting position), and at the same time, space for performing the maintenance work on the other measurement unit can be obtained as widely as possible.

Figure 8:
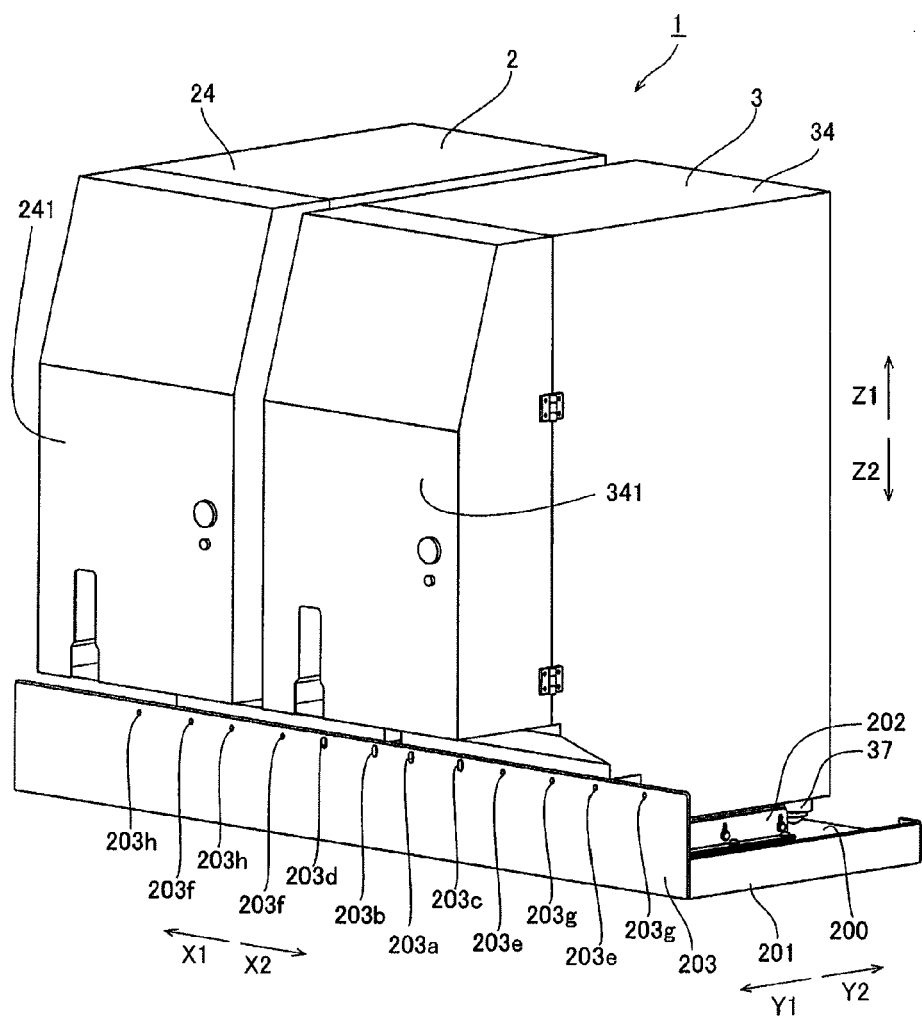
FIG. 8 is a perspective view illustrating the base of the blood analyzer according to the embodiment shown in FIG. 1.

As shown in FIG. 8, the first measurement unit 3 and the second measurement unit 2 are each configured to be fixed to the base 200 also by a front face fixing member 203 provided at the front side of the base 200 (arrow Y1 direction side). Formed in the front face fixing member 203 are: a first positioning hole 203a, a second positioning hole 203b, a third positioning hole 203c, and a fourth positioning hole 203d, each of which has an elongated shape; and a pair of first fixing holes 203e, a pair of second fixing holes 203f, a pair of third fixing holes 203g, and a pair of fourth fixing holes 203h, each of which has a round shape. The first measurement unit 3 is configured to be positioned in the first setting position when a protrusion (not shown) provided on the front face (on the arrow Y1 direction side) of the first measurement unit 3 is inserted into the first positioning hole 203a. Also, the first measurement unit 3 is configured to be positioned in the third setting position when the protrusion (not shown) thereof is inserted into the third positioning hole 203c. Similarly, the second measurement unit 2 is configured to be positioned in the second setting position or in the fourth setting position when a protrusion (not shown) provided on the front face (on the arrow Y1 direction side) of the second measurement unit 2 is inserted into the second positioning hole 203b or into the fourth positioning hole 203d, respectively. In this manner, positioning of each of the first measurement unit 3 and the second measurement unit 2 can be readily performed. The pair of first fixing holes 203e and the pair of third fixing holes 203g are configured to be used as screw holes for fixing the first measurement unit 3 in the first setting position and in the third setting position, respectively. Further, the pair of second fixing holes 203f and the pair of fourth fixing holes 203h are configured to be used as screw holes for fixing the second measurement unit 2 in the second setting position and in the fourth setting position, respectively.

As shown in FIGS. 2 and 3, the sample transporting apparatus 4 includes: an unanalyzed rack holder 41 capable of holding a plurality of racks 101 each accommodating sample containers 100 that contain unanalyzed samples; an analyzed rack holder 42 capable of holding a plurality of racks 101 each accommodating sample containers 100 that contain samples having been analyzed; a rack transporter 43 for horizontally and rectilinearly moving a rack 101 in the arrow X1 and X2 directions; a bar code reader 44; a presence/absence detection sensor 45 for detecting presence/absence of a sample container 100; and a rack sending out section 46 for moving the rack 101 to the inside of the analyzed rack holder 42.

The unanalyzed rack holder 41 has a rack feeder 411, and is configured such that the racks 101 held by the unanalyzed rack holder 41 are pushed, one by one, onto the rack transporter 43 by the rack feeder 411 moving in the arrow Y2 direction. The rack feeder 411 is configured to be driven by a stepping motor (not shown) provided below the unanalyzed rack holder 41. Further, the unanalyzed rack holder 41 has a restricting portion 412 (see FIG. 3) near the rack transporter 43, and is configured to restrict, by the restricting portion 412, the movement of the racks 101 such that once a rack 101 is pushed onto the rack transporter 43, the rack 101 does not return to the inside of the unanalyzed rack holder 41.

The analyzed rack holder 42 has a restricting portion 421 (see FIG. 3) near the rack transporter 43, and is configured to restrict, by the restricting portion 421, the movement of the racks 101 such that once a rack 101 is moved to the inside of the analyzed rack holder 42, the rack 101 does not return to the rack transporter 43.

In the present embodiment, as shown in FIG. 2, the rack transporter 43 is configured to transport the rack 101, thereby disposing a predetermined sample container 100, which is held in the rack, in the first loading position 43a at which the predetermined sample container is loaded into the first measurement unit 3 disposed in the first setting position, and disposing a predetermined sample container 100, which is held in the rack, in the second loading position 43b at which the predetermined sample container is loaded into the second measurement unit 2 disposed in the second setting position. The rack transporter 43 is also configured to be able to transport each sample container 100 to a sample presence/absence detection position 43c at which the presence/absence detection sensor 45 confirms presence or absence of each sample container 100, and to transport each sample container 100 to a reading position 43d at which the bar code reader 44 reads the bar code 100b of each sample container 100 (see FIG. 4). Further, in the below-described maintenance measurement mode, the rack transporter 43 is configured to be able to transport a predetermined sample container 100, which is held in the rack, to a third loading position 43e at which the predetermined sample container is loaded into the first measurement unit 3 disposed in the third setting position shown in FIG. 7, and transport a predetermined sample container 100, which is held in the rack, to a fourth loading position 43f at which the predetermined sample container is loaded into the second measurement unit 2 disposed in the fourth setting position shown in FIG. 6. Further, the rack transporter 43 is configured to be able to transport all the sample containers 100 (ten containers), which the rack 101 can hold, to any of the first loading position 43a, the second loading position 43b, the third loading position 43e, and the fourth loading position 43f.

In addition, the rack transporter 43 is configured to, as a result of the control apparatus 5 executing a below-described sampler operation process program 54c (see FIG. 12), transport a predetermined sample container 100 to a predetermined position, based on a transporting distance from a reference position to the predetermined position, the transporting distance being set by the sampler operation process program 54c. To be more specific, a rear edge of the rack 101 (an edge of the arrow X2 direction side of the rack 101) in a position on the rack transporter 43, into which position the racks 101 are fed from the unanalyzed rack holder 41 (hereinafter, referred to as a rack feeding position), is set as the reference position. Based on this, the sampler operation process program 54c presets the transporting distance to the predetermined position. In the case where a predetermined sample container 100 is transported to the third loading position 43e during the maintenance measurement mode, the transporting distance, which is currently set as a distance from the reference position to the first loading position 43a, is changed to a distance from the reference position to the third loading position 43e, whereby the rack transporter 43 is enabled to transport the predetermined sample container 100 to the third loading position 43e. The transporting of a predetermined sample container 100 to the fourth loading position 43f is also enabled when the transporting distance, which is currently set as a distance from the reference position to the second loading position 43b, is changed to a distance from the reference position to the fourth loading position 43f, whereby the rack transporter 43 is enabled to transport the predetermined sample container 100 to the fourth loading position 43f. Note that the third loading position 43e is located so as to be shifted from the first loading position 43a in the arrow X2 direction by a distance equivalent to four sample containers 100 held in the rack 101. Also, the fourth loading position 43f is located so as to be shifted from the second loading position 43b in the arrow X1 direction by a distance equivalent to four sample containers 100 held in the rack 101.

Figure 9:
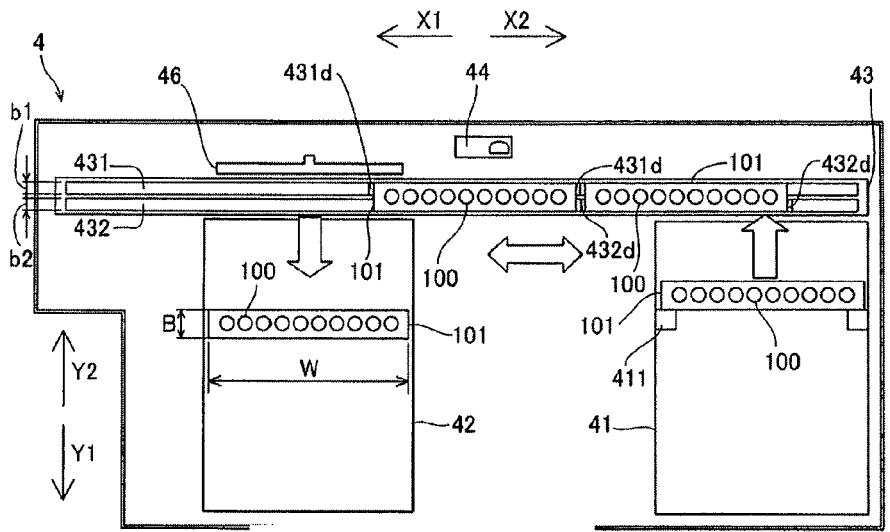
FIG. 9 is a plan view illustrating the sample transporting apparatus of the blood analyzer according to the embodiment shown in FIG. 1.
Figure 10:
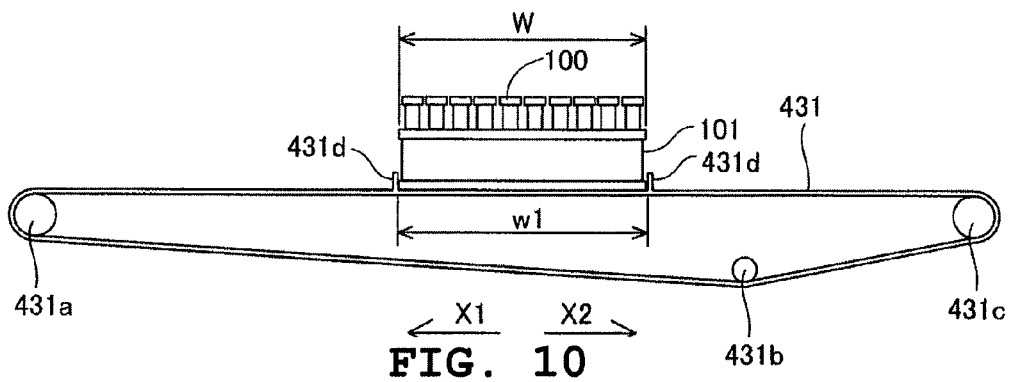
FIG. 10 is a side view illustrating the sample transporting apparatus of the blood analyzer according to the embodiment shown in FIG. 1.
Figure 11:
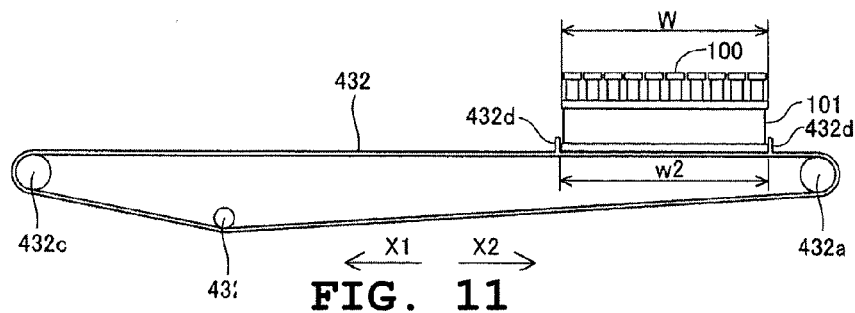
FIG. 11 is a side view illustrating the sample transporting apparatus of the blood analyzer according to the embodiment shown in FIG. 1.

As shown in FIG. 9, the rack transporter 43 has two belts that are a first belt 431 and a second belt 432 capable of moving independently of each other. A width b1 of the first belt 431 in the arrow Y1 direction and a width b2 of the second belt 432 in the arrow Y2 direction are each equal to or smaller than the half of a width B of the rack 101 in the arrow Y1 and Y2 directions. This allows the first belt 431 and the second belt 432 to be arranged in parallel to each other and not to be displaced from the width B of the rack 101 when the rack transporter 43 transports the rack 101. Further, as shown in FIGS. 10 and 11, the first belt 431 and the second belt 432 are each formed in an annular shape, and are provided so as to be wound around rollers 431a to 431c and rollers 432a to 432c, respectively. The outer periphery of the first belt 431 has two protrusions 431d formed thereon and the outer periphery of the second belt 432 has two protrusions 432d formed thereon, such that an interval between the protrusions 431d and an interval between the protrusions 432d have an inner width w1 (see FIG. 10) and an inner width w2 (see FIG. 11), respectively, which are both slightly greater (e.g., by approximately 1 mm) than a width W of the rack 101 in the arrow X1 and X2 directions. The first belt 431 is configured to move, when holding the rack 101 between the protrusions 431d, the rack 101 in the arrow X1 or X2 direction as a result of being moved around the rollers 431a to 431c by a stepping motor 431e (see FIG. 3). Also, the second belt 432 is configured to move, when holding the rack 101 between the protrusions 432d, the rack 101 in the arrow X1 or X2 direction as a result of being moved around the rollers 432a to 432c by a stepping motor 432e (see FIG. 3). The first belt 431 and the second belt 432 are configured to be able to move the rack 101 independently of each other.

Figure 4:
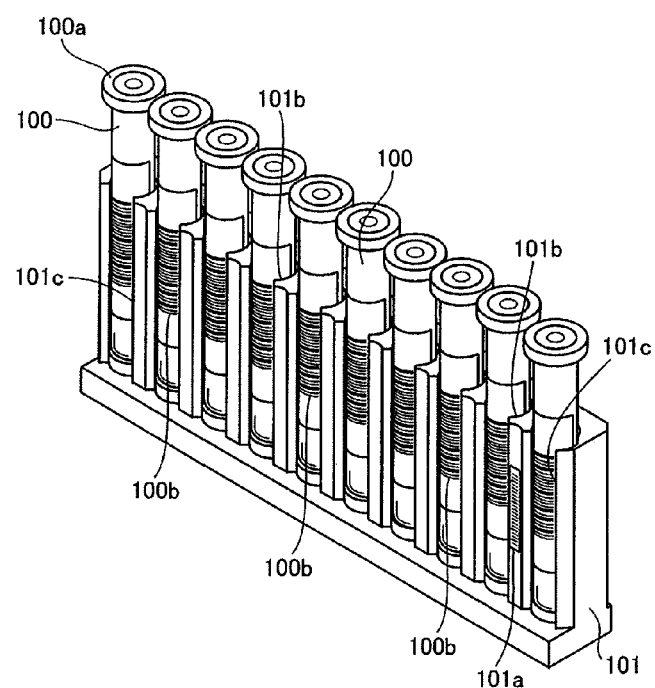
FIG. 4 is a perspective view showing a rack and sample containers of the blood analyzer according to the embodiment shown in FIG. 1.

The bar code reader 44 is configured to read the bar code 100b of each sample container 100 shown in FIG. 4 and a bar code 101a affixed to the rack 101. The bar code reader 44 is configured to read the bar code 100b of a target sample container 100 accommodated in the rack 101 when the target sample container 100 is being horizontally rotated by a rotator (not shown) without being removed from the rack 101. Accordingly, even in the case where the bar code 100b of the sample container 100 is affixed at the opposite side to the bar code reader 44, the bar code 100b can be caused to face the bar code reader 44. Note that the bar code 101a is uniquely assigned to each rack 101, and used for, e.g., managing analysis results of the samples.

The presence/absence detection sensor 45 has a curtain-like contact segment 451 (see FIG. 3), a light emitting element for emitting light (not shown), and a light receiving element (not shown). The presence/absence detection sensor 45 is configured such that the contact segment 451 is bent when contacted by a detection subject, and as a result, the light emitted from the light emitting element is reflected by the contact segment 451 and then incident on the light receiving element. Accordingly, when a sample container 100 which is accommodated in the rack 101 and which is a detection subject passes below the presence/absence detection sensor 45, the contact segment 451 is bent by the sample container 100. As a result, the presence of the sample container 100 can be detected.

The rack sending out section 46 is disposed so as to be opposed to the analyzed rack holder 42 while having the rack transporter 43 positioned therebetween, and is configured to horizontally move in the arrow Y1 direction. The rack sending out section 46 is configured to push, by horizontally moving in the arrow Y1 direction, the rack 101 that is placed, on the rack transporter 43, in a position between the analyzed rack holder 42 and the rack sending out section 46 (hereinafter, referred to as a rack sending out position), toward the analyzed rack holder 42 side.

Figure 12:
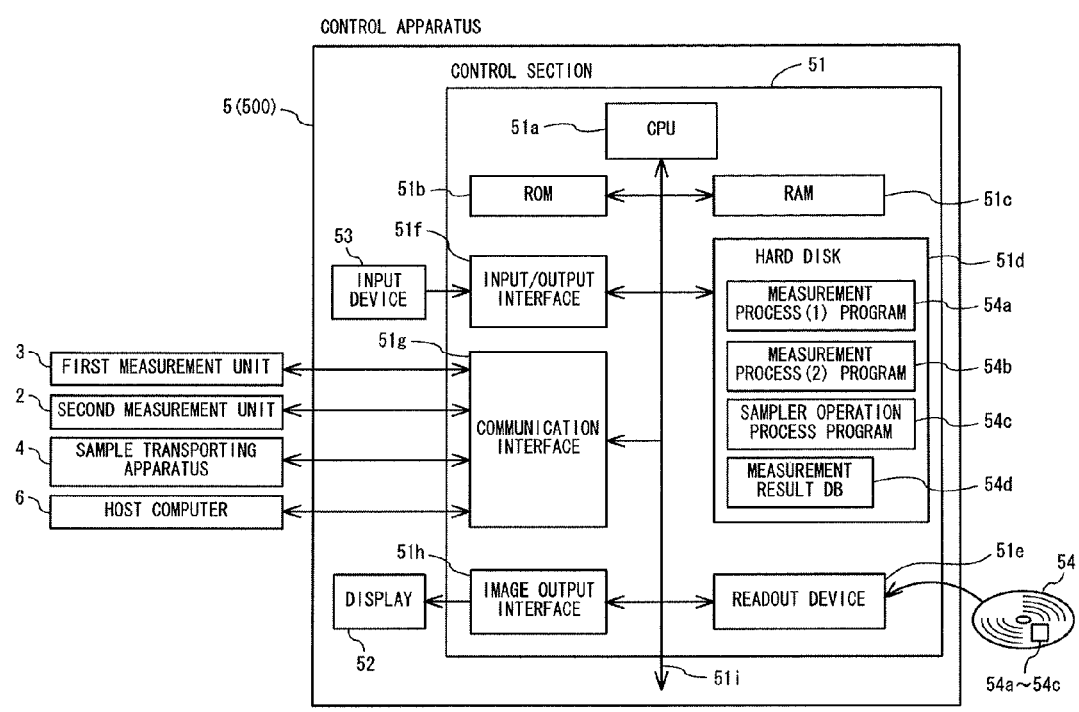
FIG. 12 is a block diagram illustrating a control apparatus of the blood analyzer according to the embodiment shown in FIG. 1.

As shown in FIGS. 1, 2 and 12, the control apparatus 5 is structured as a personal computer (PC) or the like. The control apparatus 5 includes: a control section 51 (see FIG. 12) including a CPU, ROM, RAM and the like; a display 52; and an input device 53. The display 52 is provided so as to display analysis results and the like that are obtained by analyzing digital signal data transmitted from the first measurement unit 3 and the second measurement unit 2.

As shown in FIG. 12, the control apparatus 5 is structured as a computer 500 of which the main components are the control section 51, the display 52, and the input device 53. The main components of the control section 51 are a CPU 51a, a ROM 51b, a RAM 51c, a hard disk 51d, a readout device 51e, an input/output interface 51f, a communication interface 51g, and an image output interface 51h. The CPU 51a, ROM 51b, RAM 51c, hard disk 51d, readout device 51e, input/output interface 51f, communication interface 51g, and the image output interface 51h are connected to each other via a bus 51i.

The CPU 51a is capable of executing computer programs stored in the ROM 51b and computer programs loaded into the RAM 51c. The computer 500 acts as the control apparatus 5 through execution, by the CPU 51a, of application programs 54a, 54b and 54c that are described below.

The ROM 51b is structured as a mask ROM, PROM, EPROM, EEPROM or the like, and stores computer programs to be executed by the CPU 51a and stores data to be used by the computer programs.

The RAM 51c is structured as an SRAM, DRAM or the like. The RAM 51c is used for reading computer programs stored in the ROM 51b and the hard disk 51d. The RAM 51c is used as a work area for the CPU 51a when the CPU 51a executes these computer programs.

Installed in the hard disk 51d are: various computer programs to be executed by the CPU 51a, such as an operating system and application programs; and data to be used for executing these computer programs. A measurement process (1) program 54a for the first measurement unit 3, a measurement process (2) program 54b for the second measurement unit 2, and a sampler operation process program 54c for the sample transporting apparatus 4 are also installed in the hard disk 51d. Through the execution of these application programs 54a to 54c by the CPU 51a, operations of respective components of the first measurement unit 3, the second measurement unit 2, and the sample transporting apparatus 4 are controlled. Further, a measurement result database 54d is also installed in the hard disk 51d.

The readout device 51e is structured as a flexible disc drive, CD-ROM drive, DVD-ROM drive or the like. The readout device 51e is capable of reading computer programs or data, which are stored in a portable storage medium 54. The portable storage medium 54 stores therein the application programs 54a to 54c. The computer 500 is capable of reading the application programs 54a to 54c from the portable storage medium 54 to install the read application programs 54a to 54c in the hard disk 51d.

Note that the application programs 54a to 54c can be provided to the computer 500 not only via the portable storage medium 54, but also from an external device via a telecommunication line (regardless of whether wired or wireless), which external device is communicably connected to the computer 500 by the telecommunication line. For example, the application programs 54a to 54c are stored in a hard disk of a server computer on the Internet. The computer 500 can access the server computer, and download the application programs 54a to 54c from the server computer to install the application programs 54a to 54c in the hard disk 51d.

Also, an operating system that provides a graphical user interface environment, for example, Windows (registered trademark) manufactured and sold by Microsoft Corporation, is installed in the hard disk 51d. In the description below, it is assumed that the application programs 54a to 54c run on the operating system.

For example, the input/output interface 51f is configured as: a serial interface such as USB, IEEE1394 or RS-232C; a parallel interface such as SCSI, IDE or IEEE1284; or an analogue interface including a D/A converter, A/D converter and the like. The input device 53 is connected to the input/output interface 51f. A user can input data to the computer 500 by using the input device 53.

The communication interface 51g is an Ethernet (registered trademark) interface, for example. The computer 500 is capable of transmitting/receiving data to/from the first measurement unit 3, the second measurement unit 2, the sample transporting apparatus 4, and the host computer 6 via the communication interface 51g, using a predetermined communication protocol.

The image output interface 51h is connected to the display 52 that is structured with LCD, CRT or the like. Video signals corresponding to image data, which are supplied from the CPU 51a, are outputted to the display 52. The display 52 is configured to display an image (screen) in accordance with the inputted video signals.

The control section 51 having the above configuration is configured to use measurement results transmitted from the first measurement unit 3 and the second measurement unit 2 to analyze components that are analysis subjects, and obtain results of the analysis (red blood count, platelet count, amount of hemoglobin, white blood count, and the like).

As shown in FIG. 4, in the rack 101, ten container accommodating portions 101b are formed so as to be able to accommodate ten sample containers 100 in line. Further, the container accommodating portions 101b are each provided with an opening 101c such that the bar code 100b of each sample container 100 accommodated therein can be visually recognized.

Figure 13:
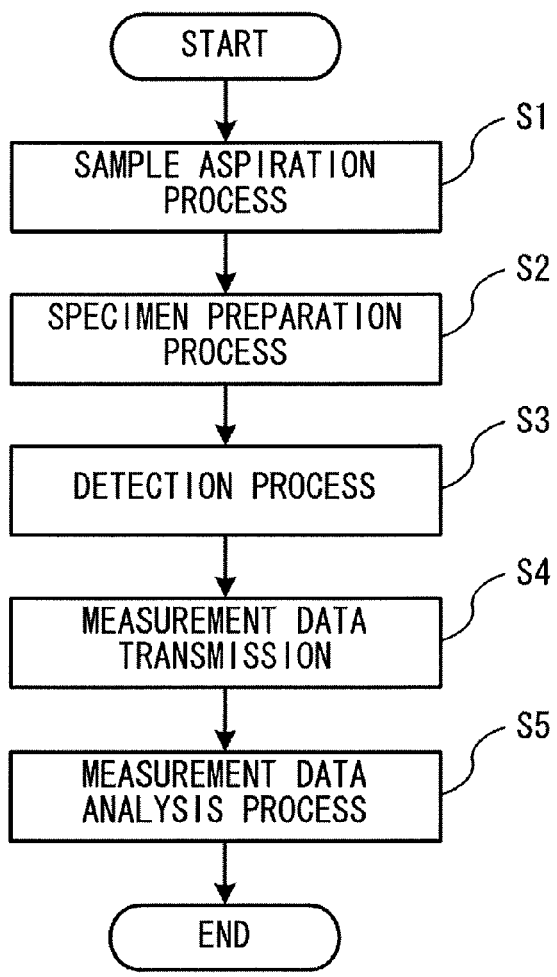
FIG. 13 is a flowchart illustrating operations that are performed, in measurement processes based on measurement process programs, by the blood analyzer according to the embodiment shown in FIG. 1.

FIG. 13 is a flowchart illustrating operations that are performed, in measurement processes based on the measurement process programs, by the blood analyzer according to the embodiment of the present invention. Described next with reference to FIG. 13 are operations that are performed, in measurement processes based on the measurement process programs 54a and 54b, by the blood analyzer 1 according to the present embodiment.

First, at step S1, the sample aspirator 31 aspirates a sample from a sample container 100 having been transported to the aspirating position 700 (see FIG. 2). Then, at step S2, a detection specimen is prepared from the aspirated sample by the specimen preparation section 32. At step S3, the detector 33 detects, from the detection specimen, the components that are analysis subjects. Then, at step S4, measurement data is transmitted from the first measurement unit 3 to the control apparatus 5. Thereafter, at step S5, the control section 51 analyzes, based on the measurement data transmitted from the first measurement unit 3, the components that are analysis subjects. The analysis of the sample is completed at step S5, and the operations end.

Figure 14:
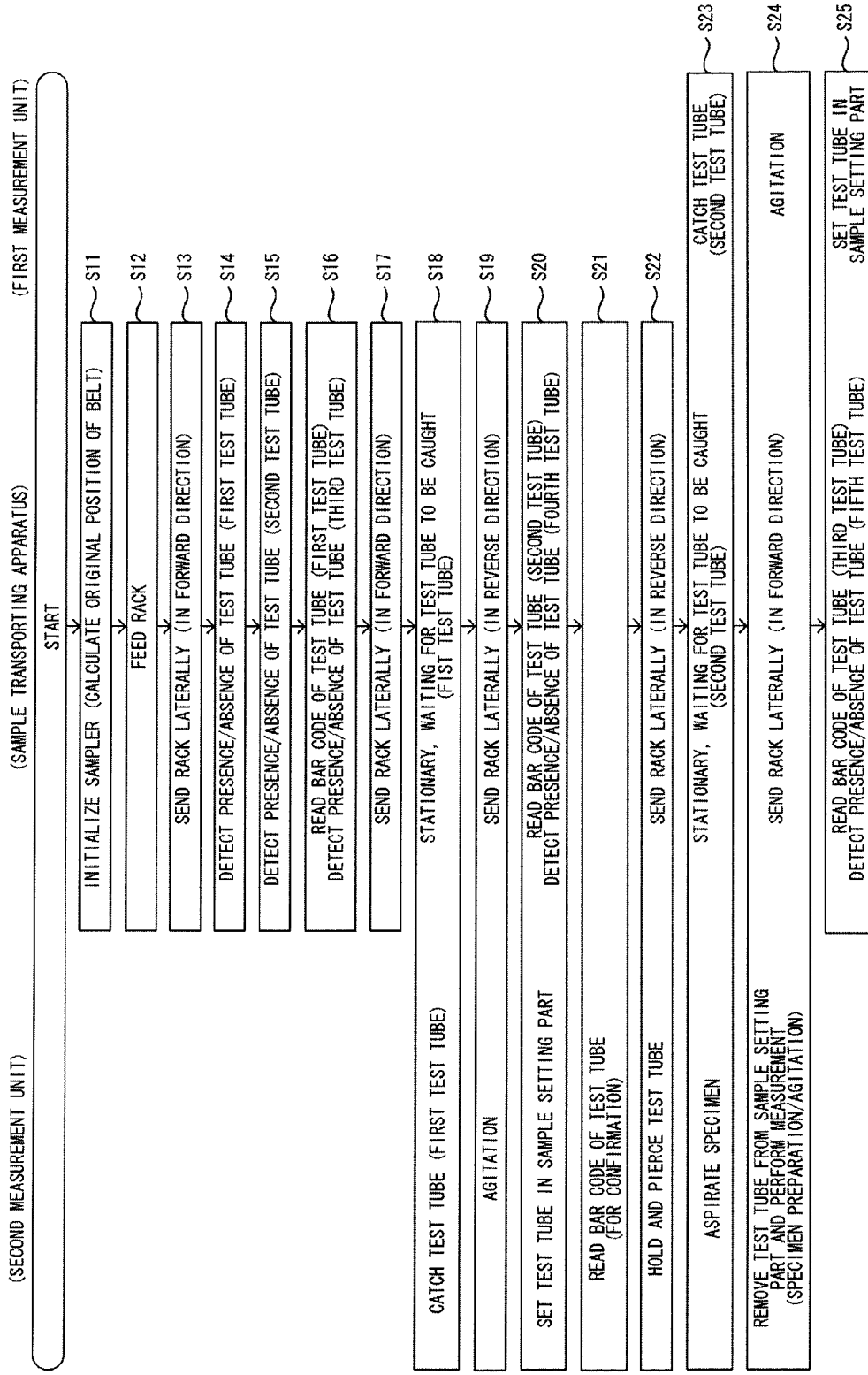
FIG. 14 is a flowchart illustrating the details of operations that are performed by the blood analyzer according to the embodiment shown in FIG. 1 in a normal mode based on a measurement process (1) program, a measurement process (2) program, and a sampler operation process program.
Figure 15:
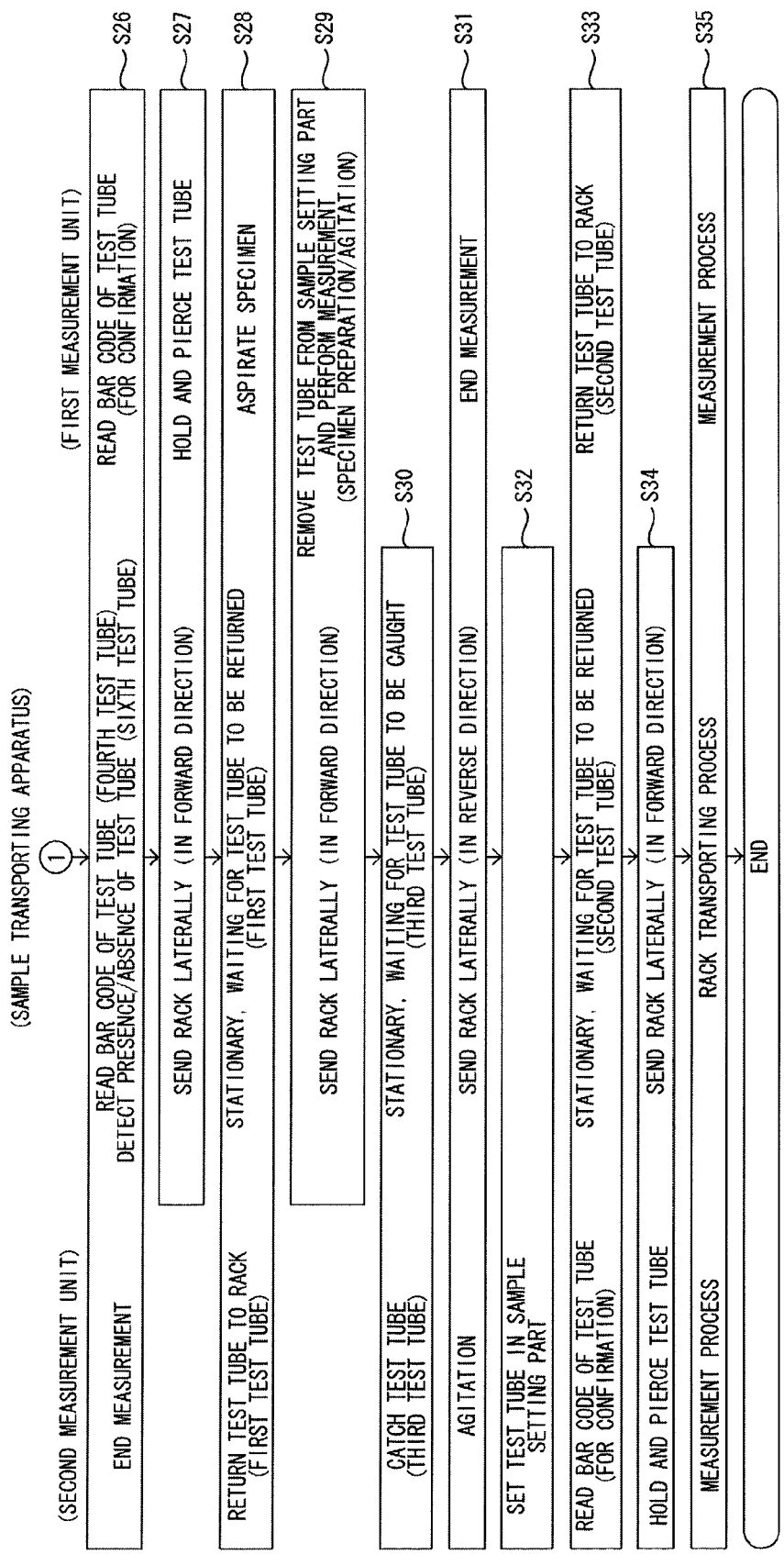
FIG. 15 is a flowchart illustrating the details of operations that are performed by the blood analyzer according to the embodiment shown in FIG. 1 in the normal mode based on the measurement process (1) program, the measurement process (2) program, and the sampler operation process program.
Figure 16:
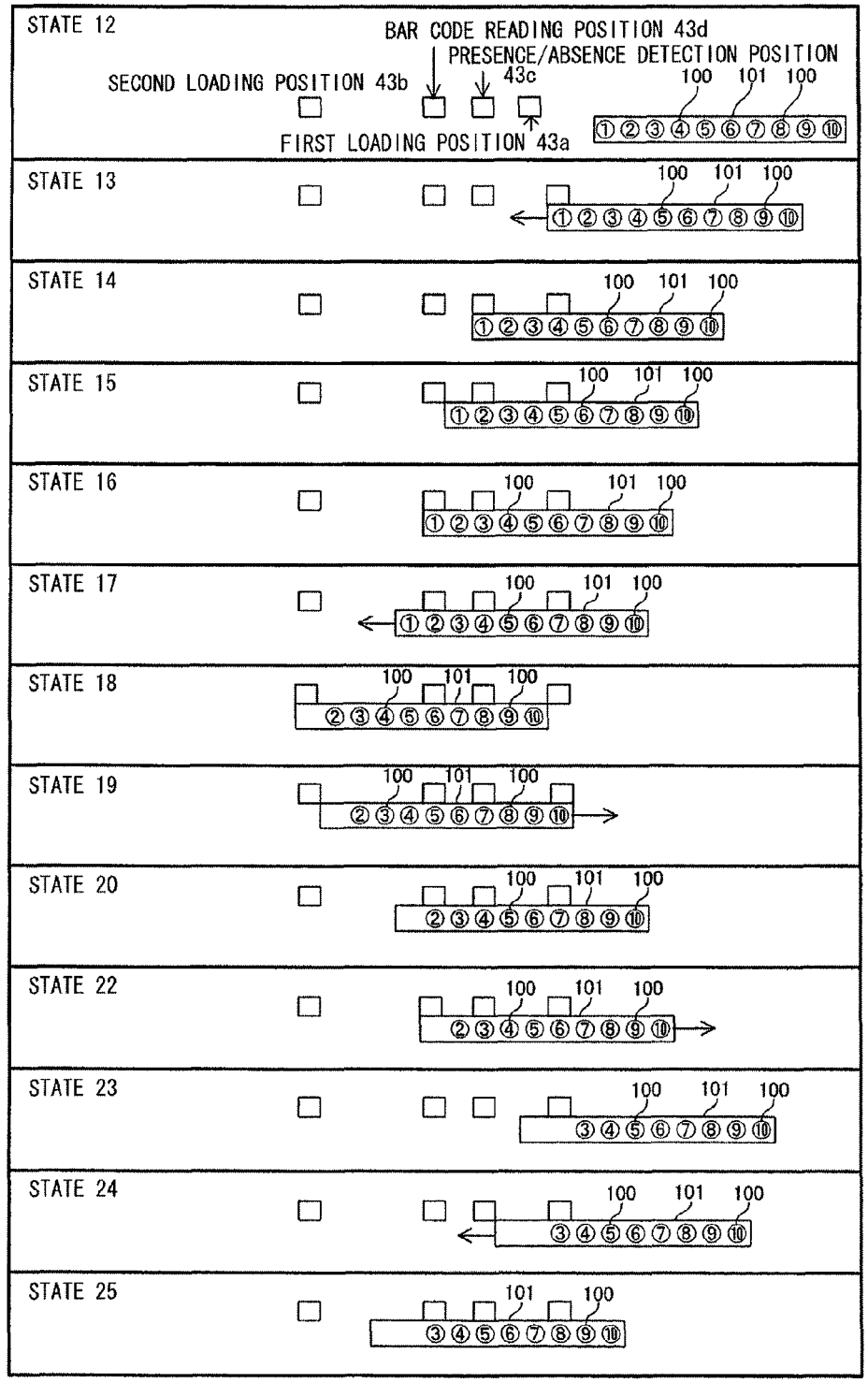
FIG. 16 shows positional relationships between sample containers and each position in the blood analyzer according to the embodiment shown in FIG. 1 in the normal mode.
Figure 17:
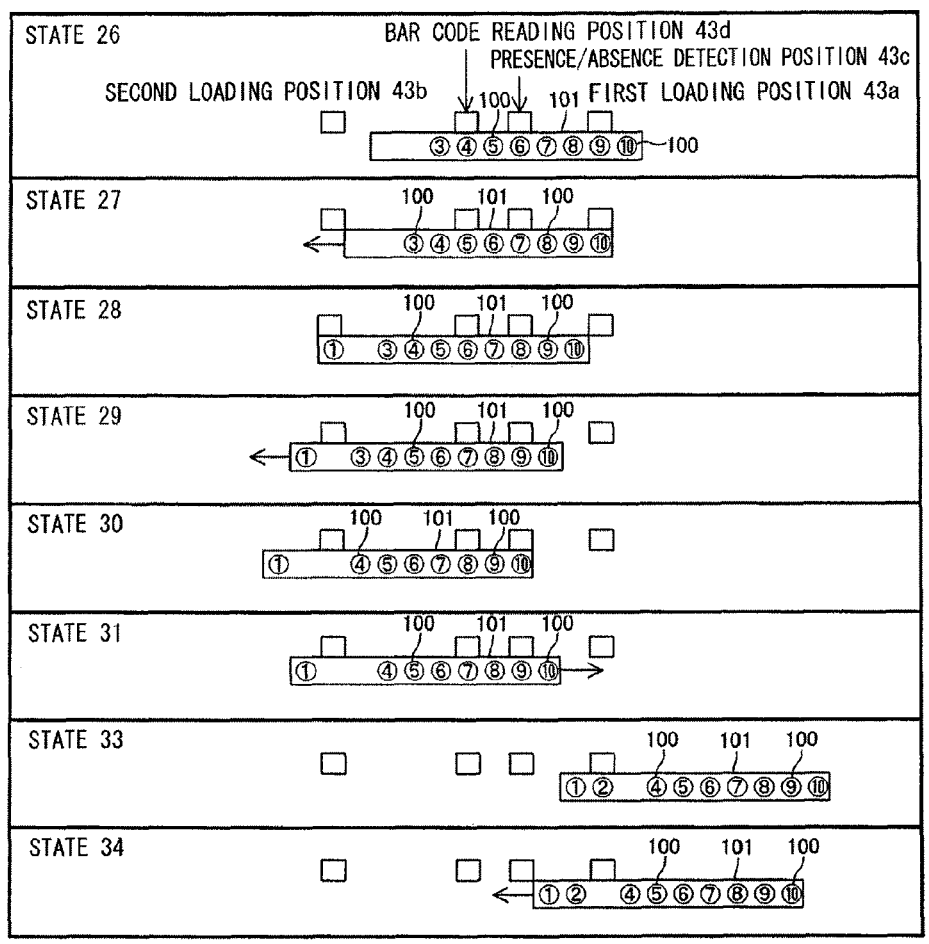
FIG. 17 shows positional relationships between the sample containers and each position in the blood analyzer according to the embodiment shown in FIG. 1 in the normal mode.

FIGS. 14 and 15 are flowcharts each illustrating the details of the operations that are performed by the blood analyzer in the normal mode based on the measurement process (1) program, the measurement process (2) program, and the sampler operation process program. FIGS. 16 and 17 each show positional relationships between sample containers and each position in the blood analyzer according to the embodiment of the present invention. Described next with reference to FIGS. 14 to 17 is a series of operations that are performed by the first measurement unit 3, the second measurement unit 2, and the sample transporting apparatus 4 when the blood analyzer 1 according to the present embodiment is in the normal mode. Note that the flowcharts in FIGS. 14 and 15 each show, in the right side rows thereof, the operations performed based on the measurement process (1) program 54a, and show, on the left side rows thereof, the operations performed based on the measurement process (2) program 54b, and show, in the central rows thereof, the operations performed based on the sampler operation process program 54c. Further, in FIGS. 16 and 17, state numbers indicating positional relationships between the sample containers 100 and each position are provided so as to correspond to step numbers shown in FIGS. 14 and 15. For example, positional relationships between the sample containers 100 and each position in STATE 13 of FIG. 16 are positional relationships between the sample containers 100 and each position at step S13 of FIG. 14. Note that as shown in FIGS. 14 and 15, the measurement process (1) program 54a, the measurement process (2) program 54b, and the sampler operation process program 54c are practically executed in parallel in the normal mode of the blood analyzer 1.

First, when the blood analyzer 1 is started by a user, the sample transporting apparatus 4 is initialized at step S11. At this point, the protrusions 431d of the first belt 431 are moved to predetermined positions. These positions are set as original positions of the first belt 431. At step S12, the two protrusions 431d are moved to positions corresponding to the rack feeding position. Then, the rack 101 is fed between the two protrusions 431d of the first belt 431. At this point, positional relationships between the sample containers 100 and each position are as shown in STATE 12 of FIG. 16. Note that in the description below, positional relationships between the sample containers 100 and each position in each state shown in FIGS. 16 and 17 are not described.

At step S13, the rack 101 is moved in the direction of the second measurement unit 2 (forward direction). At step S14, presence or absence of the first sample container 100 accommodated in the rack 101 is detected at the sample presence/absence detection position 43c by the presence/absence detection sensor 45. Then, at step S15, presence or absence of the second sample container 100 is detected at the sample presence/absence detection position 43c. At step S16, the bar code 100b of the first sample container 100 is read at the reading position 43d by the bar code reader 44, and presence or absence of the third sample container 100 is detected at the sample presence/absence detection position 43c. Note that detection results obtained by the presence/absence detection sensor 45 and bar code information read by the bar code readers 44, 256 and 356 are transmitted to the host computer 6 at any time as necessary. At step S17, the rack 101 is moved such that the first sample container 100 is disposed in the second loading position 43b. At this point, the bar code 101a of the rack 101 is read by the bar code reader 44. Then, at step S18, the first sample container 100 having reached the second loading position 43b is removed from the rack 101 by the hand part 251 of the second measurement unit 2. At this point, the rack 101 is stationary such that the first sample container 100 is disposed in the second loading position 43b. At step S19, the sample in the first sample container 100 held by the hand part 251 is agitated in the second measurement unit 2, and the rack 101 from which the first sample container 100 has been removed is moved in a reverse direction that is the opposite direction to the forward direction.

At step S20, in the second measurement unit 2, the first sample container 100 is set into the sample setting part 255a, and the bar code 100b of the second sample container 100 in the rack 101 is read, and presence or absence of the fourth sample container 100 is detected. At step S21, in the second measurement unit 2, the bar code 100b of the first sample container 100 is read by the bar code reader 256. At step S22, the first sample container 100 held by the sample setting part 255a is held at the aspirating position 600 by the pair of chuck parts 261, and the piercer 211 of the sample aspirator 21 penetrates through the sealing cap 100a of the first sample container 100. Here, the rack 101 is moved such that the second sample container 100 is disposed in the first loading position 43a. Thereafter, at step S23, in the second measurement unit 2, the sample contained in the first sample container 100 is aspirated by the sample aspirator 21, and the second sample container 100 is removed at the first loading position 43a from the rack 101 by the hand part 351.

At step S24, in the second measurement unit 2, the first sample container 100 is removed from the sample setting part 255a by the hand part 251, and specimen preparation, agitation, and analysis are performed on the sample aspirated by the sample aspirator 21. Further, in the first measurement unit 3, the sample contained in the second sample container 100 held by the hand part 351 is agitated, and the rack 101 is moved in the forward direction. At step S25, in the first measurement unit 3, the second sample container 100 is set into the sample setting part 355a, and the bar code 100b of the third sample container 100 in the rack 101 is read, and presence or absence of the fifth sample container 100 is detected. Then, at step S26, in the second measurement unit 2, the measurement of the sample contained in the first sample container 100 ends, and in the first measurement unit 3, the bar code 100b of the second sample container 100 is read by the bar code reader 356. Further, the bar code 100b of the fourth sample container 100 in the rack 101 is read, and presence or absence of the sixth sample container 100 is detected. Note that "ending of the measurement of a sample" in this description means the completion of measurement data transmission at step S4 shown in FIG. 13. That is, at step S26, even when the measurement of the sample contained in the first sample container 100 has ended, the process of analyzing the measurement data at step S5 has not been completed yet.

At step S27, the second sample container 100 held by the sample setting part 355a of the first measurement unit 3 is held at the aspirating position 700 by the pair of chuck parts 361, and the piercer 311 of the sample aspirator 31 penetrates through the sealing cap 100a of the second sample container 100. Here, the rack 101 is moved in the forward direction. Then, at step S28, the first sample container 100 is returned from the second measurement unit 2 to a container accommodating portion 101b of the rack 101, which is the original storing position of the first sample container 100, and in the first measurement unit 3, the sample contained in the second sample container 100 is aspirated by the sample aspirator 31.

At step S29, in the first measurement unit 3, the second sample container 100 is removed from the sample setting part 355a by the hand part 351, and specimen preparation, agitation, and analysis are performed on the sample aspirated by the sample aspirator 31. Further, the rack 101 is moved in the forward direction. At step S30, the third sample container 100 is removed from the rack 101 by the hand part 251 of the second measurement unit 2. At this point, the rack 101 is stationary such that the third sample container 100 is disposed in the second loading position 43b. At step S31, in the second measurement unit 2, the sample contained in the third sample container 100 held by the hand part 251 is agitated, and the rack 101 is moved in the reverse direction. Also, in the first measurement unit 3, measurement of the sample contained in the second sample container 100 ends.

Then, at step S32, in the second measurement unit 2, the third sample container 100 is set into the sample setting part 255a. At step S33, in the second measurement unit 2, the bar code 100b of the third sample container 100 is read by the bar code reader 256. Also, the second sample container 100 is returned from the first measurement unit 3 to a container accommodating portion 101b of the rack 101, which is the original storing position of the second sample container 100. At step S34, the third sample container 100 is held at the aspirating position 600 by the pair of chuck parts 261. Also, the piercer 211 of the sample aspirator 21 penetrates through the sealing cap 100a of the third sample container 100. Further, the rack 101 is moved in the forward direction. Thereafter, for the other sample containers 100, the first measurement unit 3 and the second measurement unit 2 perform the measurement processes and the sample transporting apparatus 4 performs the process of transporting the rack 101 in the same manner as described above. Therefore, in order to simplify the drawings, it is assumed that the predetermined processes are performed in the respective positions at step S35. Accordingly, the series of operations performed in the normal mode by the first measurement unit 3, the second measurement unit 2, and the sample transporting apparatus 4 continue to be performed.

Figure 18:
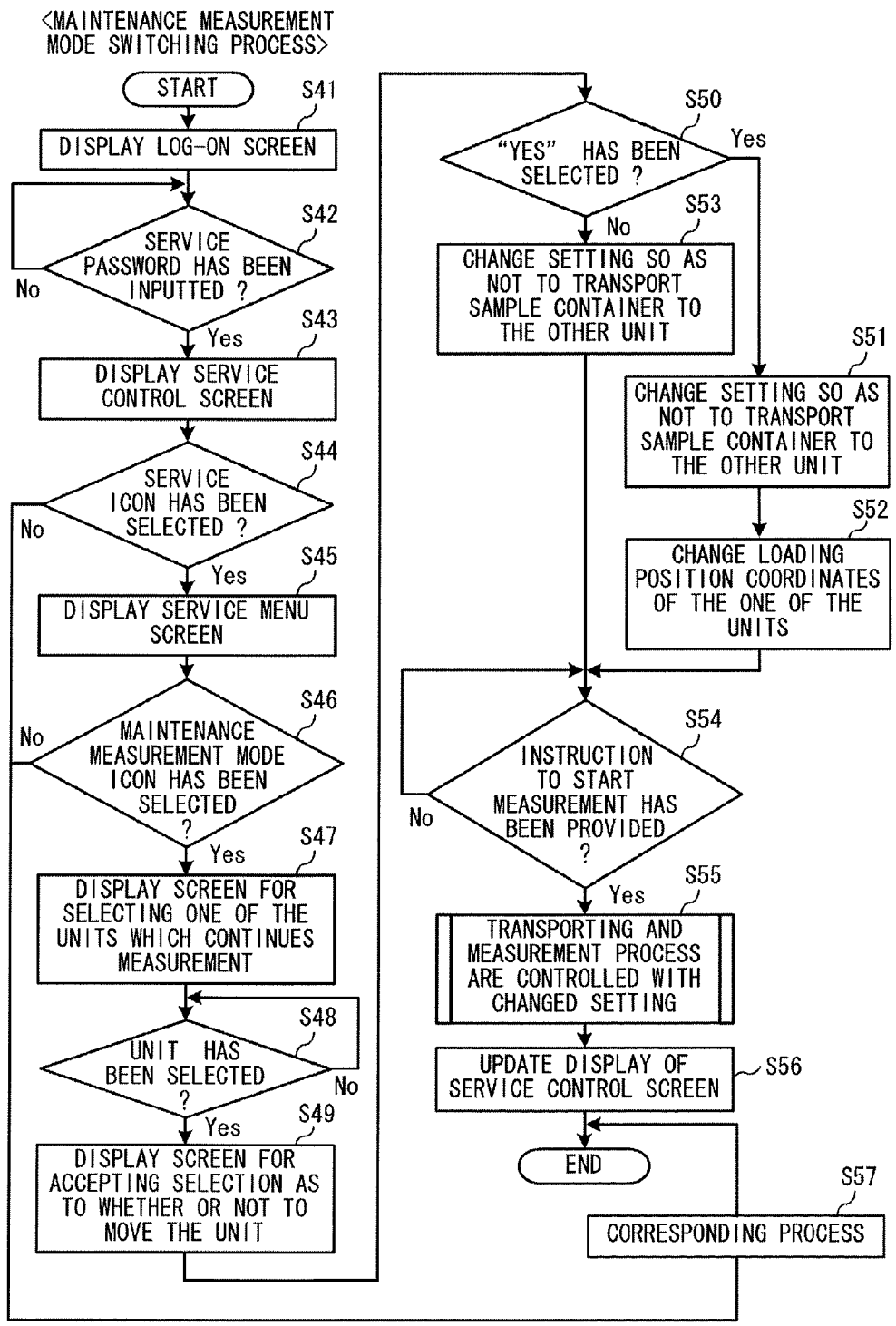
FIG. 18 is a flowchart illustrating operations that are performed in a maintenance measurement mode switching process by the blood analyzer according to the embodiment shown in FIG. 1.

FIG. 18 is a flowchart illustrating operations that are performed in a maintenance measurement mode switching process by the blood analyzer according to the embodiment shown in FIG. 1. FIGS. 19 to 23 each show a screen that is displayed on the display of the blood analyzer according to the embodiment shown in FIG. 1. Described next with reference to FIGS. 18 to 23 are operations that are performed in the maintenance measurement mode switching process by the blood analyzer according to the embodiment shown in FIG. 1.

Figure 19:
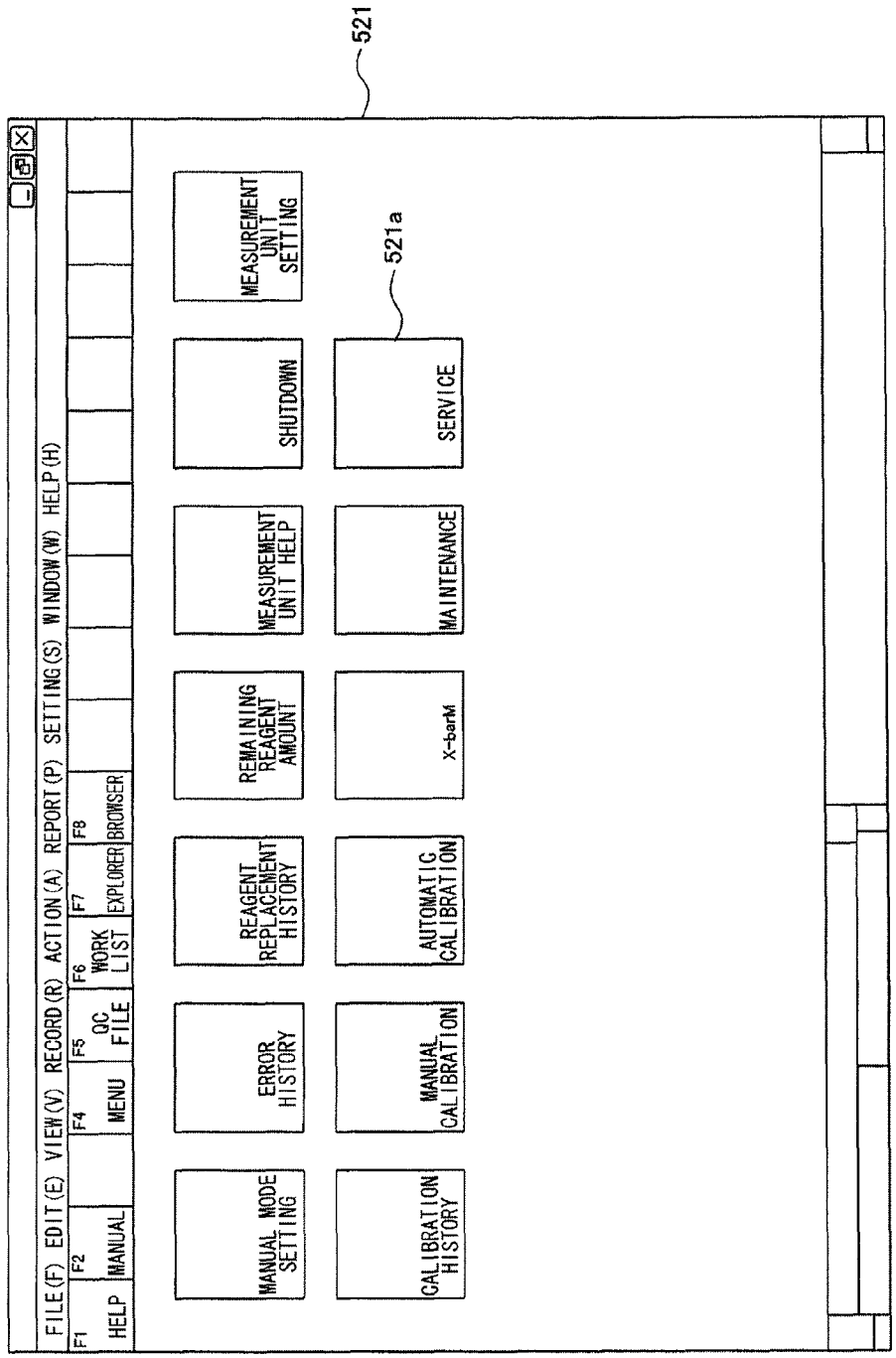
FIG. 19 shows a service control screen that is displayed on a display of the blood analyzer according to the embodiment shown in FIG. 1.

First, at step S41, a log-on screen (not shown) is displayed on the display 52, which prompts an input of a service password. Then, at step S42, the CPU 51a of the control apparatus 5 determines whether or not the service password has been inputted. This determination step is repeated until the service password in inputted. When the service password is inputted, a service control screen 521 is displayed on the display 52 at step S43 as shown in FIG. 19. The service control screen 521 shows, in a selectable manner, a plurality of icons for performing various settings and the like. One of such icons shown in the screen is a service icon 521a. Note that the service icon 521a is shown only when log-on is performed using the service password. Accordingly, only a particular person who owns the service password (e.g., a service person who performs maintenance work) can select the service icon 521a.

Figure 20:
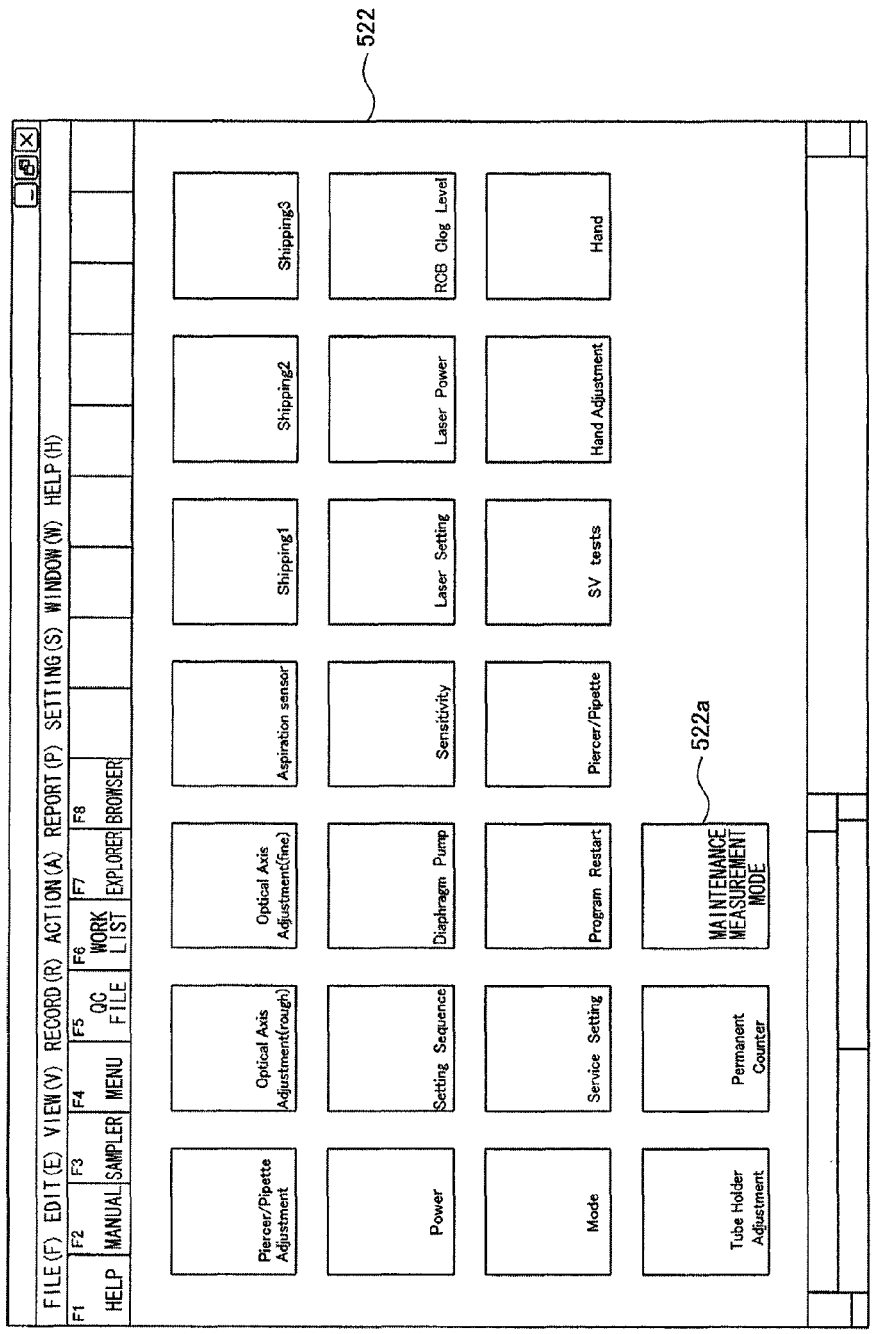
FIG. 20 shows a service menu screen that is displayed on the display of the blood analyzer according to the embodiment shown in FIG. 1.
Figure 21:
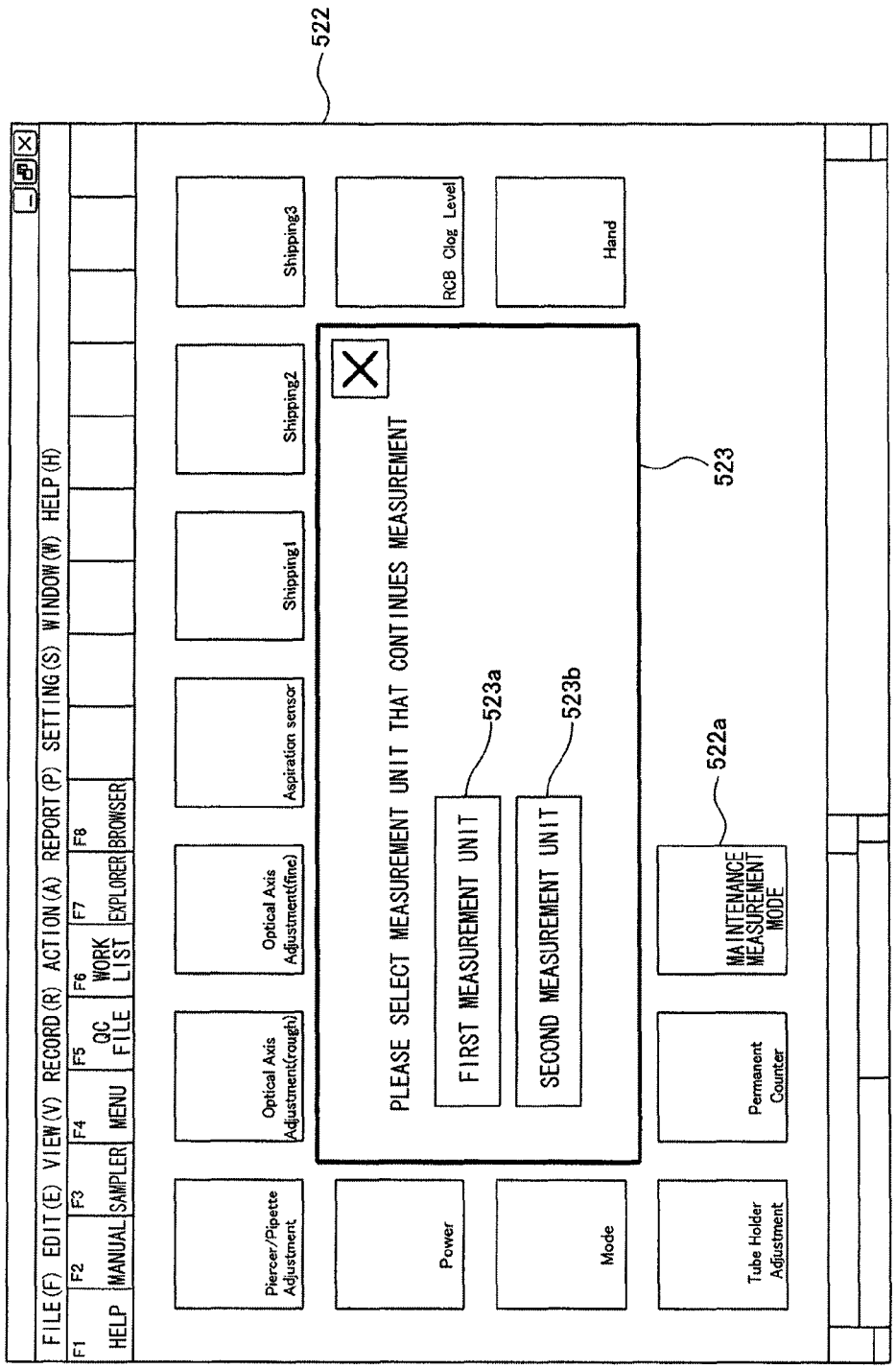
FIG. 21 shows a measurement unit selection screen that is displayed on the display of the blood analyzer according to the embodiment shown in FIG. 1.

At step S44, it is determined whether or not the service icon 521a has been selected. When a different icon from the service icon 521a is selected, a process corresponding to the selected icon is performed at step S57, and then the operations end. When the service icon 521a is selected, a service menu screen 522 is displayed at step S45 as shown in FIG. 20. The service menu screen 522 shows a plurality of icons in a selectable manner, including a maintenance measurement mode icon 522a. Then, at step S46, the CPU 51a determines whether or not the maintenance measurement mode icon 522a has been selected. When a different icon from the maintenance measurement mode icon 522a is selected, the processing proceeds to step S57. When the maintenance measurement mode icon 522a is selected, a measurement unit selection screen 523 is displayed over the service menu screen 522 at step S47. Note that as a result of the maintenance measurement mode icon 522a being selected, the mode is switched from the normal mode to the maintenance measurement mode. The measurement unit selection screen 523 shows a first measurement unit button 523a and a second measurement unit button 523b, and also shows a message that prompts selection of one of the measurement units, which is to continue the measurement during the maintenance measurement mode.

Figure 22:
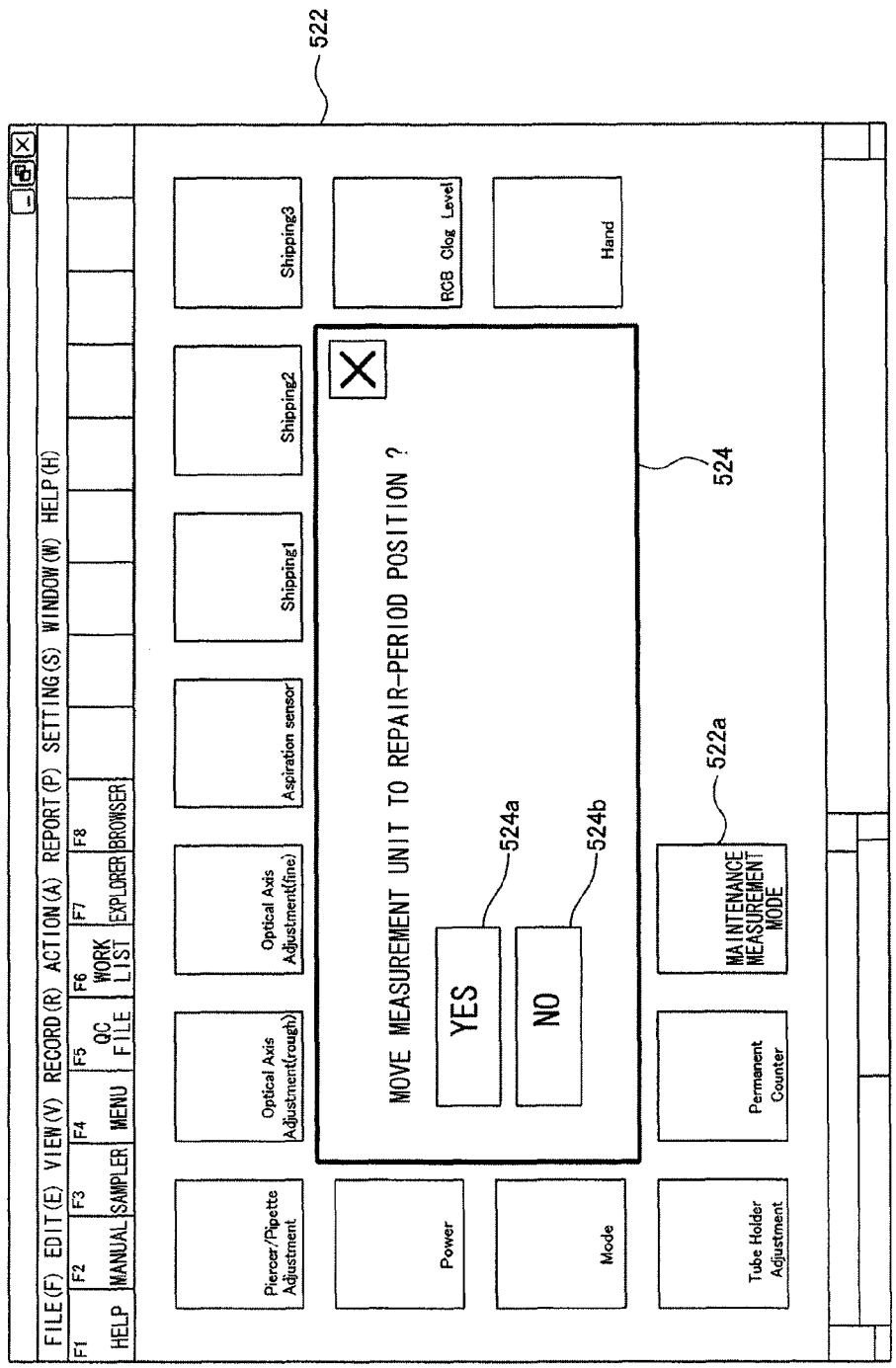
FIG. 22 shows a movement confirmation screen that is displayed on the display of the blood analyzer according to the embodiment shown in FIG. 1.

At step S48, it is determined whether or not one of the measurement units has been selected. This determination step is repeated until one of the measurement units is selected. When one of the measurement units is selected, a movement confirmation screen 524 for confirming whether or not to move the selected one of the measurement units is displayed over the service menu screen 522 at step S49 as shown in FIG. 22. The movement confirmation screen 524 shows a "YES" button 524a and a "NO" button 524b. At step S50, it is determined whether or not the "YES" button 524a has been selected. Here, the "YES" button 524a is selected in the case where the measurement unit, which is selected as a measurement unit to continue the measurement, is moved from the proper position of the normal mode (the first setting position or the second setting position). To be specific, in the case of the first measurement unit 3, the "YES" button 524a is selected when the first measurement unit 3 is moved from the first setting position to the third setting position. In the case of the second measurement unit 2, the "YES" button 524a is selected when the second measurement unit 2 is moved from the second setting position to the fourth setting position. In the case of not changing the position of the measurement unit, which is selected as a measurement unit to continue the measurement, from the proper position of the normal mode (the first setting position or the second setting position), the "NO" button 524b is selected.

In the case where the "YES" button 524a is selected, a setting is performed at step S51 such that sample containers 100 are not transported to the other measurement unit (the measurement unit that is a subject of maintenance work) that has not been selected as a measurement unit to continue the measurement. To be specific, in the case where the second measurement unit 2 is selected as a measurement unit to continue the measurement, a setting is performed such that sample containers 100 are not transported to the first loading position 43a or the third loading position 43e, which are positions each for supplying a sample to the first measurement unit 3. In the case where the first measurement unit 3 is selected as a measurement unit to continue the measurement, a setting is performed such that sample containers 100 are not transported to the second loading position 43b or the fourth loading position 43f, which are positions each for supplying a sample to the second measurement unit 2.

Then, at step S52, a setting is changed to change the position at which a sample is supplied to the measurement unit that is to continue the measurement. To be specific, in the case where the second measurement unit 2 is to continue the measurement, the position at which a sample is supplied to the second measurement unit 2 (i.e., loading position coordinates) is changed from the second loading position 43b to the fourth loading position 43f. To be more specific, based on the sampler operation process program 54c, a setting is changed such that the transporting distance is changed from the one between the reference position and the second loading position 43b to the one between the reference position and the fourth loading position 43f. In this manner, the position at which a sample is supplied to the second measurement unit 2 (i.e., loading position coordinates) is changed from the second loading position 43b to the fourth loading position 43f. Note that in the case where the first measurement unit 3 is to continue the measurement, the position at which a sample is supplied to the first measurement unit 3 (i.e., loading position coordinates) is changed from the first loading position 43a to the third loading position 43e in the same manner as described above.

Figure 23:
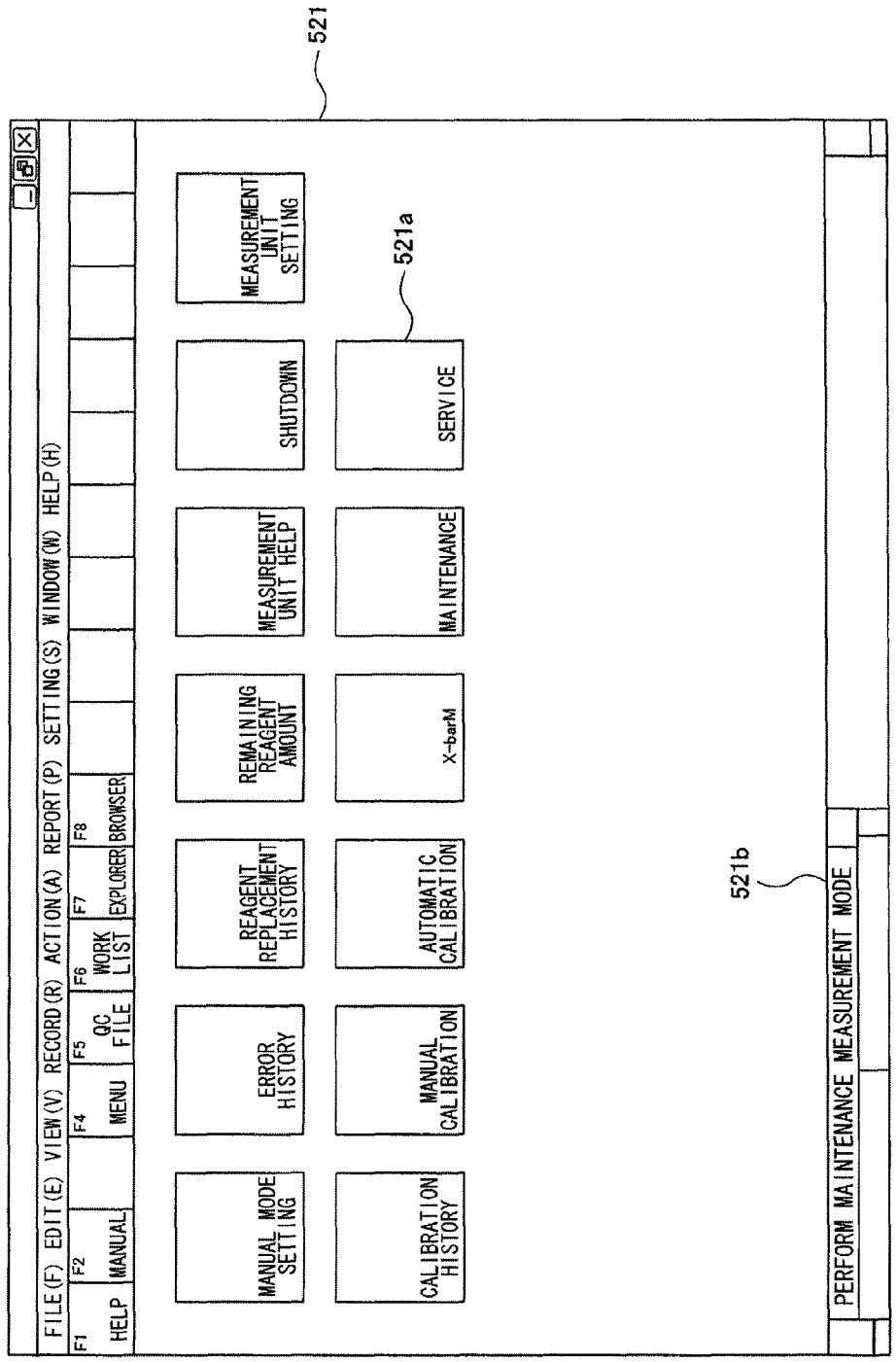
FIG. 23 shows a service control screen that is displayed on the display of the blood analyzer according to the embodiment shown in FIG. 1.

Meanwhile, when the "NO" button 524b is selected, a setting is performed at step S53 in the same manner as the above step S51 such that sample containers 100 are not transported to the other measurement unit (the measurement unit that is a subject of maintenance work) that has not been selected as a measurement unit to continue the measurement. Thereafter, it is determined at step S54 whether or not a measurement start instruction has been provided. This determination step is repeated until the measurement start instruction is provided. When the measurement start instruction has been provided, the transporting operation and the measurement process operation are performed at step S55 with the changed setting. Then, at step S56, as shown in FIG. 23, the service control screen 521 shows, in an area 521b provided at a lower left portion thereof, a message informing that the current mode is the maintenance measurement mode. Thereafter, the operations end.

Figure 24:
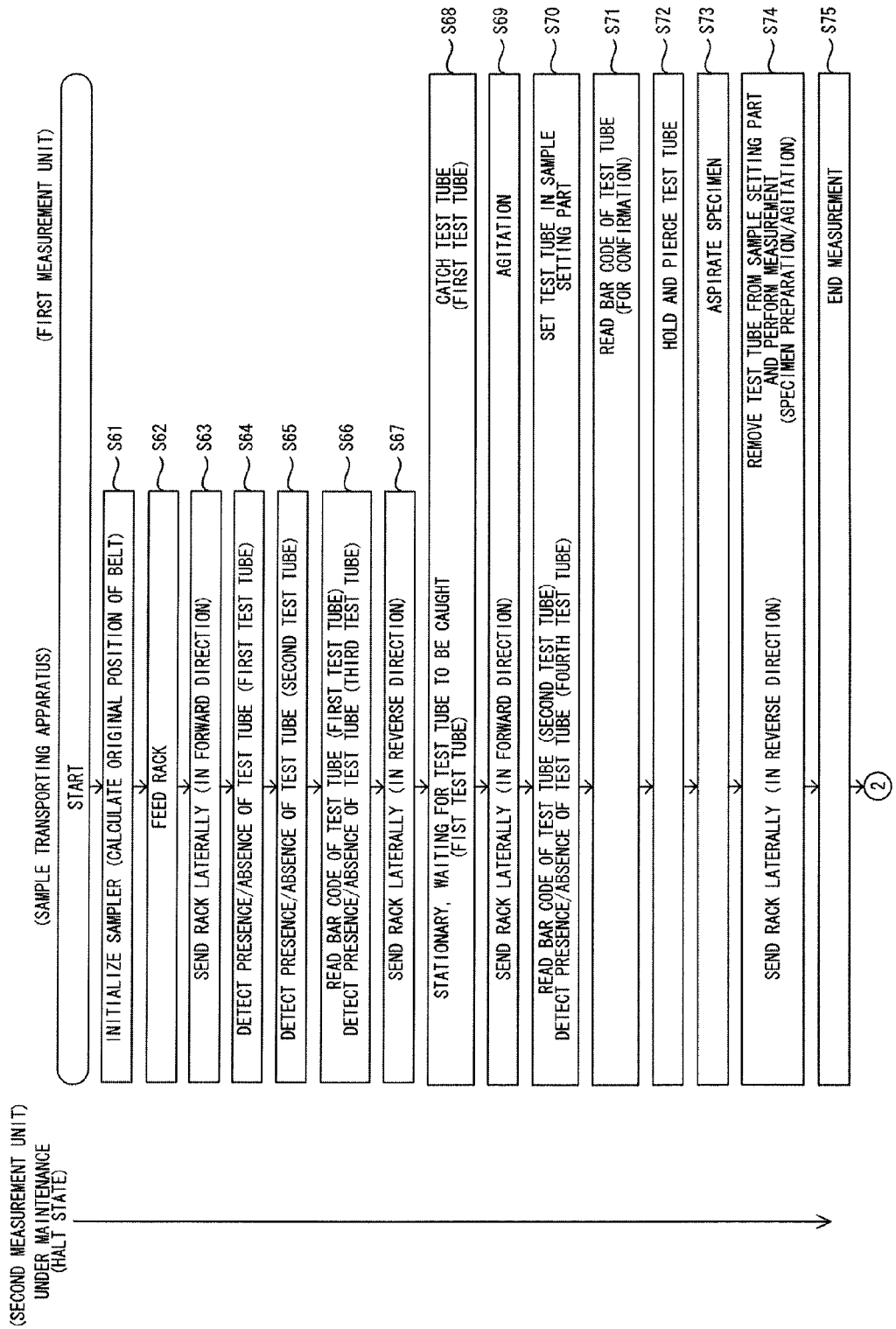
FIG. 24 is a flowchart illustrating the details of operations that are performed by the blood analyzer according to the embodiment shown in FIG. 1 in a maintenance measurement mode based on the measurement process (1) program, the measurement process (2) program, and the sampler operation process program.
Figure 25:
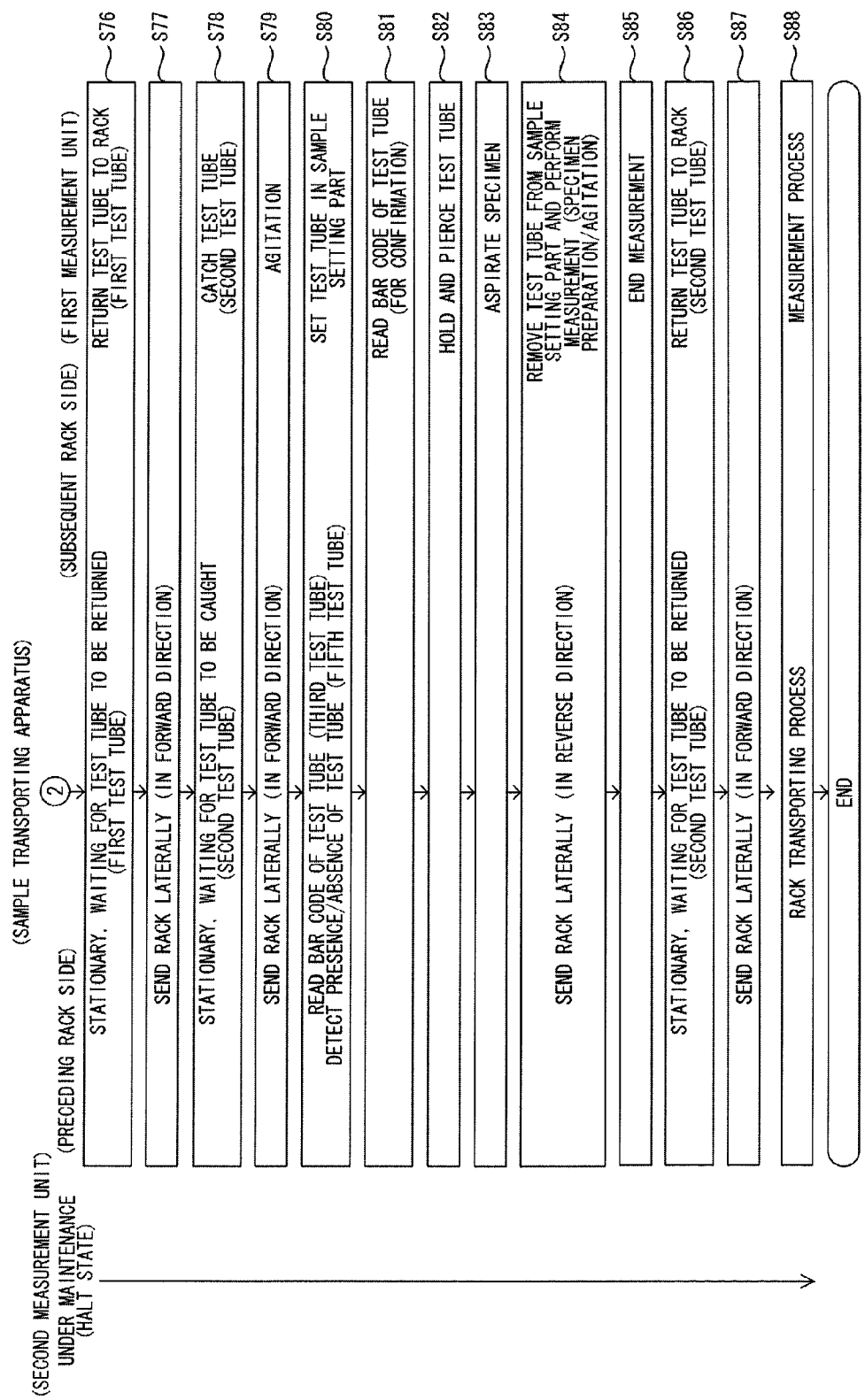
FIG. 25 is a flowchart illustrating the details of operations that are performed by the blood analyzer according to the embodiment shown in FIG. 1 in the maintenance measurement mode based on the measurement process (1) program, the measurement process (2) program, and the sampler operation process program.
Figure 26:
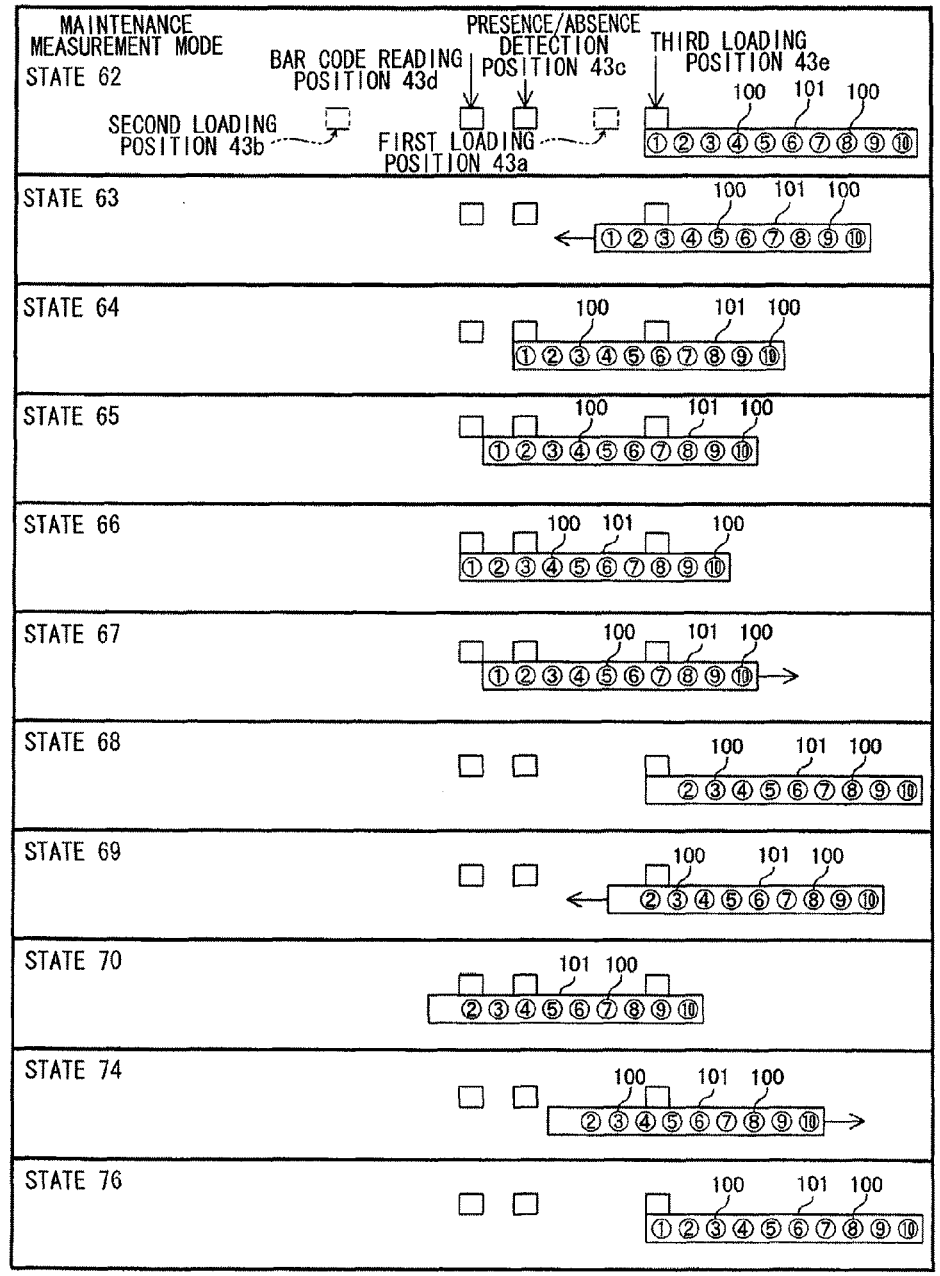
FIG. 26 shows positional relationships between sample containers and each position in the blood analyzer according to the embodiment shown in FIG. 1 in the maintenance measurement mode.
Figure 27:
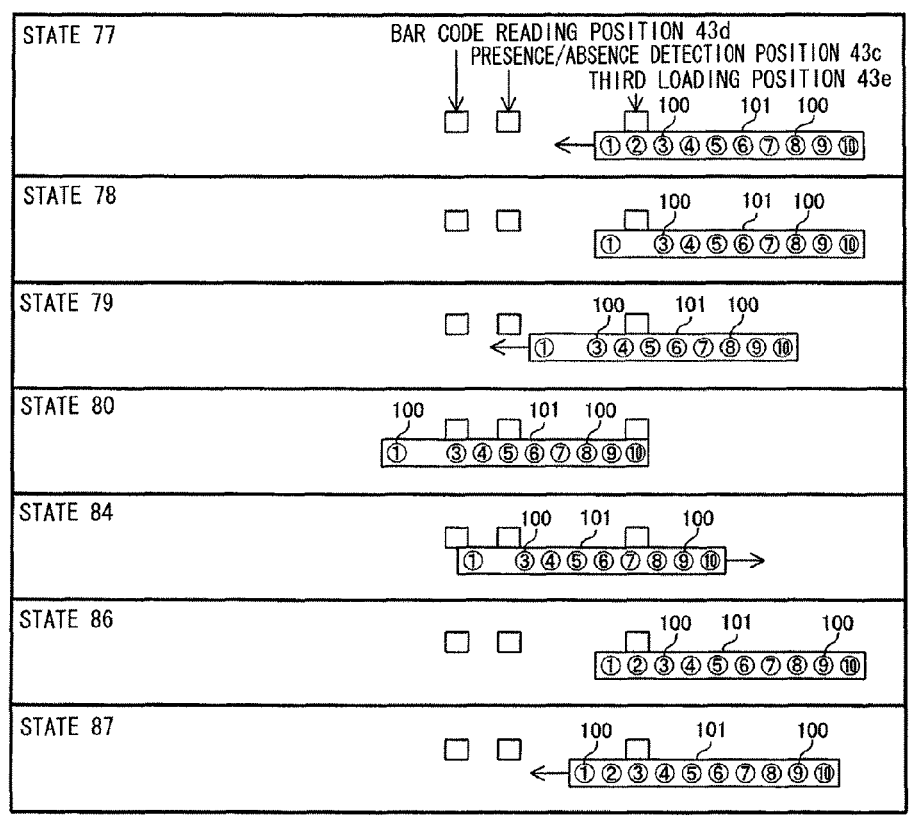
FIG. 27 shows positional relationships between the sample containers and each position in the blood analyzer according to the embodiment shown in FIG. 1 in the maintenance measurement mode.

FIGS. 24 and 25 are flowcharts each illustrating the details of operations that are performed by the blood analyzer in the maintenance measurement mode based on the measurement process (1) program, the measurement process (2) program, and the sampler operation process program. FIGS. 26 and 27 each show positional relationships, in the maintenance measurement mode, between sample containers and each position in the blood analyzer according to the embodiment of the present invention. Described next with reference to FIGS. 24 to 27 is a series of operations that are performed at step S55 of FIG. 18 by the first measurement unit 3, the second measurement unit 2, and the sample transporting apparatus 4 during the maintenance measurement mode. Hereinafter, described is a case where the first measurement unit 3 has been selected at step S48 of FIG. 18 as a measurement unit to continue the measurement, and the "YES" button 524a has been selected at step S50 of FIG. 18 (i.e., a case where the first measurement unit 3 is to be moved). That is, as shown in FIG. 7, the second measurement unit 2 is in a state where maintenance work is performable thereon and the first measurement unit 3 is disposed in the third setting position. In FIGS. 26 and 27, state numbers indicating positional relationships between the sample containers 100 and each position are provided so as to correspond to step numbers shown in FIGS. 24 and 25. As shown in FIGS. 24 and 25, the measurement process (1) program 54a, the measurement process (2) program 54b, and the sampler operation process program 54c are practically executed in parallel in the maintenance measurement mode of the blood analyzer.

First, the sample transporting apparatus 4 is initialized at step S61. To be specific, the protrusions 431d of the first belt 431 are moved to predetermined positions. These positions are set as original positions of the first belt 431. At step S62, the two protrusions 431d are moved to positions corresponding to the rack feeding position. Then, the rack 101 is fed between the two protrusions 431d of the first belt 431. At this point, positional relationships between the sample containers 100 and each position are as shown in STATE 62 of FIG. 26. Note that in the description below, positional relationships between the sample containers 100 and each position in each state shown in FIGS. 26 and 27 are not described.

At step S63, the rack 101 is moved in the forward direction (the arrow X1 direction). At step S64, presence or absence of the first sample container 100 accommodated in the rack 101 is detected at the sample presence/absence detection position 43c by the presence/absence detection sensor 45. Then, at step S65, presence or absence of the second sample container 100 is detected at the sample presence/absence detection position 43c. At step S66, the bar code 100b of the first sample container 100 is read at the reading position 43d by the bar code reader 44, and presence or absence of the third sample container 100 is detected at the sample presence/absence detection position 43c. Note that detection results obtained by the presence/absence detection sensor 45 and bar code information read by the bar code readers 44 and 356 are transmitted to the host computer 6 at any time as necessary.

In the present embodiment, at step S67, the rack 101 is moved in the reverse direction (the arrow X2 direction) such that the first sample container 100 is disposed in the third loading position 43e. To be specific, the first sample container 100, of which the bar code 100b has been read, is moved not to the sample supplying position for the second measurement unit 2 undergoing maintenance (the second loading position 43b or the fourth loading position 430 but to the third loading position 43e for the first measurement unit 3 having been moved. Further, when the rack 101 is transported in the reverse direction, the bar code 101a of the rack 101 is read by the bar code reader 44. Then, at step S68, the first sample container 100 having been moved to the third loading position 43e is removed from the rack 101 by the hand part 351 of the first measurement unit 3. At this point, the rack 101 is stationary such that the first sample container 100 is disposed in the third loading position 43e. At step S69, in the first measurement unit 3, the sample in the first sample container 100 held by the hand part 351 is agitated, and the rack 101 from which the first sample container 100 has been removed is moved in the forward direction.

At step S70, in the first measurement unit 3, the first sample container 100 is set into the sample setting part 355a, and the bar code 100b of the second sample container 100 in the rack 101 is read, and presence or absence of the fourth sample container 100 is detected. At step S71, in the first measurement unit 3, the bar code 100b of the first sample container 100 is read by the bar code reader 356. At step S72, the first sample container 100 held by the sample setting part 355a is held at the aspirating position 700 by the pair of chuck parts 361, and the piercer 311 of the sample aspirator 31 penetrates through the sealing cap 100a of the first sample container 100. Thereafter, at step S73, in the first measurement unit 3, the sample contained in the first sample container 100 is aspirated by the sample aspirator 31.

At step S74, the first sample container 100 is removed from the sample setting part 355a by the hand part 351, and specimen preparation, agitation, and analysis are performed on the sample aspirated by the sample aspirator 31. Further, the rack 101 is moved in the reverse direction. Then, at step S75, the measurement of the sample contained in the first sample container 100 ends.

Next, at step S76, the first sample container 100 in the third loading position 43e is returned from the first measurement unit 3 to a container accommodating portion 101b of the rack 101, which is the original storing position of the first sample container 100. At step S77, the rack 101 is moved in the forward direction. Then, at step S78, the second sample container 100 having been transported to the third loading position 43e is removed from the rack 101 by the hand part 351 of the first measurement unit 3. At step S79, in the first measurement unit 3, the sample in the second sample container 100 held by the hand part 351 is agitated, and the rack 101 is moved in the forward direction.

Then, at step S80, in the first measurement unit 3, the second sample container 100 is set into the sample setting part 355a, and the bar code 100b of the third sample container 100 in the rack 101 is read, and presence or absence of the fifth sample container 100 is detected. At step S81, in the first measurement unit 3, the bar code 100b of the second sample container 100 is read by the bar code reader 356. At step S82, the second sample container 100 held by the sample setting part 355a is held at the aspirating position 700 by the pair of chuck parts 361, and the piercer 311 of the sample aspirator 31 penetrates through the sealing cap 100a of the second sample container 100. Thereafter, at step S83, in the first measurement unit 3, the sample contained in the second sample container 100 is aspirated by the sample aspirator 31.

At step S84, the second sample container 100 is removed from the sample setting part 355a by the hand part 351, and specimen preparation, agitation, and analysis are performed on the sample aspirated by the sample aspirator 31. Further, the rack 101 is moved in the reverse direction. Then, at step S85, the measurement of the sample contained in the second sample container 100 ends.

Next, at step S86, the second sample container 100 in the third loading position 43e is returned from the first measurement unit 3 to a container accommodating portion 101b of the rack 101, which is the original storing position of the second sample container 100. At step S87, the rack 101 is moved in the forward direction.

Thereafter, for the third and other sample containers 100, the first measurement unit 3 performs the measurement process and the sample transporting apparatus 4 performs the process of transporting the rack 101 in the same manner as descried above. Therefore, in order to simplify the drawings, it is assumed that the predetermined processes are performed in the respective positions at step S88. Accordingly, the predetermined processes in the maintenance measurement mode continue to be performed. Note that when the second measurement unit 2 is selected at step S48 of FIG. 18 as a measurement unit to continue the measurement, the predetermined processes are performed in the same manner as described above. If the "NO" button 524b is selected at step S50 of FIG. 18, the sample containers 100 are transported to the first loading position 43a or the second loading position 43b in accordance with the measurement unit that is to continue the measurement. Then, at the first loading position 43a or the second loading position 43b, the sample containers 100 are loaded into the measurement unit.

As described above, in the present embodiment, the control apparatus 5 is provided for, when the first measurement unit 3 is moved from the first setting position at which a sample transported to the first loading position 43a can be loaded into the first measurement unit 3, to the third setting position at which a sample transported to the third loading position 43e can be loaded into the first measurement unit 3, controlling the sample transporting apparatus 4 so as to transport samples to the third loading position 43e. Accordingly, when maintenance work needs to be performed on the second measurement unit 2, the first measurement unit 3 is moved from the first setting position to the third setting position in order to obtain space for the second measurement unit 2 to move, or to obtain space for the maintenance work to be performed, and thereafter, the measurement can be performed in the first measurement unit 3 by loading the samples thereinto. Thus, when the maintenance work is performed, the sample processing can be continued while obtaining space that is sufficient for the maintenance work.

Further, in the present embodiment, the control apparatus 5 is configured to be able to, when the second measurement unit 2 is moved from the second setting position to the fourth setting position at which a sample transported to the fourth loading position 43f is loaded into the second measurement unit 2, control the sample transporting apparatus 4 so as to transport samples to the fourth loading position 43f, and control the second measurement unit 2 such that the second measurement unit 2 processes the samples, which are transported to the fourth loading position 43f to be loaded into the second measurement unit 2. Accordingly, when maintenance work needs to be performed on the first measurement unit 3, the second measurement unit 2 is moved from the second setting position to the fourth setting position in order to obtain space for the first measurement unit 3 to move, or to obtain space for the maintenance work to be performed, and thereafter, the measurement can be continued in the second measurement unit 2. Thus, the sample processing can be continued while obtaining space that is sufficient for the maintenance work, not only when the maintenance work is performed on the second measurement unit 2 but also when the maintenance work is performed on the first measurement unit 3.

Still further, in the present embodiment, the sample transporting apparatus 4 is configured to transport the samples in accordance with the set transporting distance. The control apparatus 5 is configured to control the sample transporting apparatus 4 so as to transport the samples to the third loading position 43e, in response to the setting being changed such that the transporting distance is changed from the one between the reference position and the first loading position 43a to the one between the reference position and the third loading position 43e. Accordingly, the samples can be transported to different loading positions (different loading position coordinates) only by changing the setting of the transporting distance. Thus, the position to which the samples are transported can be readily changed.

Still further, in the present embodiment, the sample transporting apparatus 4 is configured to be able to transport all the sample containers 100 (ten sample containers) held in the rack 101 to any of the first loading position 43a, the second loading position 43b, and the third loading position 43e. Accordingly, even if the first measurement unit 3 is moved to the third setting position, the measurement can be performed on all the samples held in the rack 101. This suppresses reduction in the sample processing capability.

Note that the embodiment disclosed herein is merely illustrative in all aspects and should not be recognized as being restrictive. The scope of the present invention is defined by the scope of the claims rather than by the description of the above embodiment, and includes meaning equivalent to the scope of the claims and all modifications within the scope.

For instance, the present embodiment describes the measurement units used for the blood analysis, as an example of sample processing apparatuses. However, the present invention is not limited thereto. For example, the sample processing apparatuses may be different sample processing apparatuses such as smear preparing apparatuses.

Further, as an example of a sample processing system, the present embodiment describes the blood analyzer that includes two measurement units that are the first measurement unit and the second measurement unit. However, the present invention is not limited thereto. The blood analyzer may include three or more measurement units.

Still further, the present embodiment describes a configuration example in which the CPU of the control apparatus controls both the transporting of the rack and the loading of the samples. However, the present invention is not limited thereto. The transporting of the rack and the loading of the samples may be controlled by separate control sections, respectively. In this case, the control section for controlling the transporting of the rack may be provided in the transporting apparatus, and the control section for controlling the loading of the samples may be provided in each measurement unit.

Still further, the present embodiment describes a configuration example in which an input of the service password is required in order to change the mode to the maintenance measurement mode. However, the present invention is not limited thereto. The mode may be switched to the maintenance measurement mode without requiring the input of the password.

Still further, the present embodiment describes a configuration example in which when the mode is switched to the maintenance measurement mode, the selection of the measurement unit to continue the measurement is accepted. However, the present invention is not limited thereto. For example, from among the first measurement unit and the second measurement unit, selecting a measurement unit that stops the measuring and is subjected to the maintenance work, that is, selecting a different measurement unit from a measurement unit that is moved to the third or fourth setting position and then performs the measurement, may be accepted. In this case, the control apparatus accepts a selection as to whether or not to move the measurement unit, which has not been selected, to a repair-period position (a position to which the measurement unit is moved in order to obtain space for repair work to be performed on the different measurement unit) (see FIG. 22). When accepting a selection indicating that the measurement unit is to be moved to the repair-period position, the control apparatus transports the samples to the third or fourth loading position corresponding to the measurement unit, which has not been selected. Also, the control apparatus controls the sample transporting apparatus so as not to transport the samples to the different measurement unit, which has been selected. When accepting a selection indicating that the measurement unit, which has not been selected, is not to be moved to the repair-period position, the control apparatus controls the sample transporting apparatus so as to transport the samples to the first or second loading position corresponding to the measurement unit, which has not been selected, and so as not to transport the samples to the different measurement unit, which has been selected.

Still further, as an example of a sample processing system, the present embodiment describes the blood analyzer in which both the first measurement unit and the second measurement unit are configured to be able to perform the measurement after being moved. However, the present invention is not limited thereto. As long as one of the first measurement unit and the second measurement unit is capable of continuing the measurement after being moved, the other measurement unit does not have to be capable of continuing the measurement after being moved.

Still further, the present embodiment describes an example in which the sample transporting apparatus is configured to transport a sample container to a predetermined position in accordance with the set transporting distance. However, the present invention is not limited thereto. For example, the sample transporting apparatus may be configured to transport a sample container to a predetermined position by using a position detection sensor or the like.

Still further, as an example of a transporting apparatus, the present embodiment describes the sample transporting apparatus that is capable of transporting all the sample containers (ten sample containers) held in the rack to any of the first, second, third and fourth loading positions. However, the present invention is not limited thereto. The sample transporting apparatus may be capable of transporting only a part of the plurality of samples held in the rack to the third loading position or the fourth loading position, which are sample supplying positions for a measurement unit that has been moved in order to allow maintenance work to be performed on the other measurement unit.

Still further, as an example of computer programs, the present embodiment describes three computer programs that are the measurement process (1) program, the measurement process (2) program, and the sampler operation process program. However, the present invention is not limited thereto. The computer program may be a single computer program that includes the contents of the measurement process (1) program, the measurement process (2) program, and the sampler operation process program.

Still further, the present embodiment describes an example in which the presence/absence detection position and the bar code reading position are different positions. However, the present invention is not limited thereto. The presence/absence detection position and the bar code reading position may be the same position.

What is claimed is:
1. A sample processing system comprising:
   a transporting apparatus for transporting samples to a first loading position, a second loading position, and a third loading position;
   a first sample processing apparatus capable of being set in a first setting position and a third setting position, wherein when the first sample processing apparatus is set in the first setting position, the first sample processing apparatus is capable of being loaded with the sample having been transported to the first loading position and processing the loaded sample, and when the first sample processing apparatus is set in the third setting position, the first sample processing apparatus is capable of being loaded with the sample having been transported to the third loading position and processing the loaded sample;
   a second sample processing apparatus capable of being set in a second setting position, wherein when the second sample processing apparatus is set in the second setting position, the second sample processing apparatus is capable of being loaded with the sample having been transported to the second loading position and processing the loaded sample; and
   a controller including a memory under control of a processor, the memory storing instructions enabling the processor to carry out operations comprising:
      controlling the transporting apparatus so as to transport a sample to the first loading position when the first sample processing apparatus is set in the first setting position; and controlling the transporting apparatus so as to transport a sample to the third loading position when the first sample processing apparatus is set in the third setting position.

2. The sample processing system according to claim 1, wherein
the transporting apparatus transports a sample to a fourth loading position in addition to transporting the samples to the first to third loading positions,
the second sample processing apparatus is capable of being set in a fourth setting position, wherein when the second sample processing apparatus is set in the second fourth setting position, the second sample processing apparatus is being loaded with the sample having been transported to the fourth loading position and processing the loaded sample, and
the operations further comprise:
controlling the transporting apparatus so as to transport a sample to the second loading position when the second sample processing apparatus is set in the second setting position; and
controlling the transporting apparatus so as to transport a sample to the fourth loading position when the second sample processing apparatus is set in the fourth setting position.

3. The sample processing system according to claim 2, wherein
the first sample processing apparatus is set in the third setting position by being moved from the first setting position in a direction away from the second setting position, and
the second sample processing apparatus is set in the fourth setting position by being moved from the second setting position in a direction away from the first setting position.

4. The sample processing system according to claim 2, wherein the operations further comprise:
receiving selection of a sample processing apparatus that is to process a sample, from among the first sample processing apparatus set in the third setting position and the second sample processing apparatus set in the fourth setting position;
controlling, when selection of the first sample processing apparatus is received, the transporting apparatus so as to transport a sample to the third loading position; and
controlling, when selection of the second sample processing apparatus is received, the transporting apparatus so as to transport a sample to the fourth loading position.

5. The sample processing system according to claim 1, wherein the operations further comprise:
receiving selection of one of a first mode and a second mode;
controlling, when selection of the first mode is received, the transporting apparatus so as to transport samples to the first loading position and the second loading position; and
controlling, when selection of the second mode is received, the transporting apparatus so as to transport a sample to the third loading position.

6. The sample processing system according to claim 2,
receiving selection of one of a first mode and a second mode;
receiving selection of one of the first sample processing apparatus and the second sample processing apparatus, when selection of the second mode is received;
controlling, when selection of the first sample processing apparatus is received, the transporting apparatus so as to transport samples to the third loading position or the fourth loading position; and
controlling, when selection of the second sample processing apparatus is received, the transporting apparatus so as to transport a sample to the third loading position or the fourth loading position.

7. The sample processing system according to claim 1, wherein
the transporting apparatus transports a sample in accordance with a transporting distance set by the controller,
the operations further comprise:
controlling the transporting apparatus so as to transport a sample to the first loading position, by setting a distance from a reference position to the first loading position as the transporting distance, and
controlling the transporting apparatus so as to transport a sample to the third loading position, by setting a distance from the reference position to the third loading position as the transporting distance.

8. The sample processing system according to claim 1, wherein the operations further comprise
controlling the first sample processing apparatus such that when the first sample processing apparatus is in the third setting position, the first sample processing apparatus is loaded with the sample having been transported to the third loading position and processes the loaded sample.

9. A sample processing method comprising:
transporting a sample to a first loading position;
performing loading and processing, of the sample having been transported to the first loading position, by a first sample processing apparatus that is set in a first setting position;
transporting a sample to a second loading position;
performing loading and processing, of the sample having been transported to the second loading position, by a second sample processing apparatus that is set in a second setting position;
transporting a sample to a third loading position when the first sample processing apparatus is set in a third setting position; and
performing loading and processing, of the sample having been transported to the third loading position, by the first sample processing apparatus set in the third setting position.

10. The sample processing method according to claim 9, further comprising:
transporting a sample to a fourth loading position when the second sample processing apparatus is set in a fourth setting position; and
performing loading and processing, of the sample having been transported to the fourth loading position, by the second sample processing apparatus set in the fourth setting position.

11. A computer program product for a sample processing system comprising: a transporting apparatus for transporting samples; a first sample processing apparatus for being loaded with and processing a sample; a second sample processing apparatus for being loaded with and processing a sample; and a computer, the computer program product comprising a computer readable medium for storing instructions enabling the computer to carry out operations comprising:
controlling the transporting apparatus so as to transport a sample to a first loading position;
controlling the first sample processing apparatus set in a first setting position such that the first sample processing apparatus is loaded with the sample having been transported to the first loading position and processes the loaded sample;

controlling the transporting apparatus so as to transport a sample to a second loading position;

controlling the second sample processing apparatus set in a second setting position such that the second sample processing apparatus is loaded with the sample having been transported to the second loading position and processes the loaded sample;

controlling the transporting apparatus so as to transport a sample to a third loading position when the first sample processing apparatus is set in a third setting position; and controlling the first sample processing apparatus set in the third setting position, such that the first sample processing apparatus is loaded with the sample having been transported to the third loading position and processes the loaded sample.

12. The computer program product according to claim 11, wherein the operations further comprise:

controlling the transporting apparatus so as to transport a sample to a fourth loading position when the second sample processing apparatus is set in a fourth setting position; and controlling the second sample processing apparatus set in the fourth setting position, such that the second sample processing apparatus is loaded with the sample having been transported to the fourth loading position and processes the sample.

13. The computer program product according to claim 12, wherein the operations further comprise:

receiving selection of a sample processing apparatus that is to process a sample, from among the first sample processing apparatus set in the third setting position and the second sample processing apparatus set in the fourth setting position;

controlling, when selection of the first sample processing apparatus is received, the transporting apparatus so as to transport a sample to the third loading position; and controlling, when selection of the second sample processing apparatus is received, the transporting apparatus so as to transport a sample to the fourth loading position.

14. The computer program product according to claim 11, wherein the operations further comprise:

receiving selection of one of a first mode and a second mode;

controlling, when selection of the first mode is received, the transporting apparatus so as to transport samples to the first loading position and the second loading position; and controlling, when selection of the second mode is received, the transporting apparatus so as to transport a sample to the third loading position.

15. The computer program product according to claim 12, receiving selection of one of a first mode and a second mode;

receiving selection of one of the first sample processing apparatus and the second sample processing apparatus, when selection of the second mode is received;

controlling, when selection of the first sample processing apparatus is received, the transporting apparatus so as to transport samples to the third loading position; and controlling, when selection of the second sample processing apparatus is received, the transporting apparatus so as to transport a sample to the fourth loading position.

16. The computer program product according to claim 11, wherein the transporting apparatus transports a sample in accordance with a transporting distance set by the computer, the operations further comprise:

controlling the transporting apparatus so as to transport a sample to the first loading position, by setting a distance from a reference position to the first loading position as the transporting distance, and controlling the transporting apparatus so as to transport a sample to the third loading position, by setting a distance from the reference position to the third loading position as the transporting distance.

17. The computer program product according to claim 11, wherein the operations further comprise controlling the first sample processing apparatus such that when the first sample processing apparatus is in the third setting position, the first sample processing apparatus is loaded with the sample having been transported to the third loading position and processes the loaded sample.

* * * * *